(12) United States Patent
Dahners et al.

(10) Patent No.: US 8,870,931 B2
(45) Date of Patent: Oct. 28, 2014

(54) ANTI-UNSCREWING AND MULTI-ANGULAR FASTENING APPARATUSES AND METHODS FOR SURGICAL BONE SCREW/PLATE SYSTEMS

(75) Inventors: Laurence E. Dahners, Chapel Hill, NC (US); Nicholas F. Warner, Cummington, MA (US)

(73) Assignees: The University of North Carolina at Chapel Hill, Chapel Hill, NC (US); AngleFix Tech, LLC, Charlotte, NC (US)

( * ) Notice: Subject to any disclaimer, the term of this patent is extended or adjusted under 35 U.S.C. 154(b) by 552 days.

(21) Appl. No.: 11/726,382

(22) Filed: Mar. 21, 2007

(65) Prior Publication Data
US 2008/0234677 A1 Sep. 25, 2008

(51) Int. Cl.
| | | |
|---|---|---|
| A61B 17/80 | (2006.01) | |
| A61B 17/84 | (2006.01) | |
| A61B 17/88 | (2006.01) | |
| A61B 17/86 | (2006.01) | |
| F16B 25/00 | (2006.01) | |
| F16B 35/06 | (2006.01) | |

(52) U.S. Cl.
CPC .......... *A61B 17/8057* (2013.01); *A61B 17/861* (2013.01); *F16B 25/00* (2013.01); *A61B 17/863* (2013.01); *A61B 17/8047* (2013.01); *A61B 17/8888* (2013.01); *F16B 35/065* (2013.01); *A61B 17/888* (2013.01)
USPC .......................................... 606/289; 606/305

(58) Field of Classification Search
USPC .................. 606/280, 281, 286, 289, 291, 305
See application file for complete search history.

(56) References Cited

U.S. PATENT DOCUMENTS

| 132,946 | A | * | 11/1872 | Armstrong ..................... 411/406 |
|---|---|---|---|---|
| 1,116,532 | A | | 11/1914 | Armstrong |

(Continued)

FOREIGN PATENT DOCUMENTS

| CA | 2 626 694 | 9/2000 |
|---|---|---|
| CN | 2008/80017163.3 | 8/2010 |

(Continued)

OTHER PUBLICATIONS

International Search Report and Written Opinion dated Jul. 11, 2008.

(Continued)

*Primary Examiner* — Christian Sevilla
(74) *Attorney, Agent, or Firm* — Jenkins, Wilson, Taylor & Hunt, P.A.

(57) ABSTRACT

A fastening apparatus includes a fastener and a fastener receiving member. The apparatus enables the fastener to be affixed to the fastener receiving member at a variable insertion angle selected by the user and further provides an anti-unscrewing feature. The fastener includes an elongate section and an adjoining head section having at least one slot therein. The fastener receiving member includes one or more apertures having a contact region through which one or more corresponding fasteners can be inserted. The contact region includes a matrix of protrusions having a density and strength sufficient to render contact region tappable by the thread of the head section of the fastener. The thread on the head section is driven into the contact region at the selected insertion angle. As a result, the protrusions project into the at least one slot to prevent the fastener from backing out of the fastener receiving member. A fastener driver is also disclosed.

44 Claims, 18 Drawing Sheets

(56) References Cited

U.S. PATENT DOCUMENTS

| | | | |
|---|---|---|---|
| 1,498,040 A * | 6/1924 | Johnson | 81/53.2 |
| 1,785,847 A * | 12/1930 | Valentine | 81/441 |
| 2,248,054 A | 7/1941 | Becker | |
| 2,507,882 A * | 5/1950 | Berman | 411/417 |
| 4,877,020 A * | 10/1989 | Vich | 606/86 R |
| 5,667,513 A | 9/1997 | Torrie et al. | |
| 5,702,398 A | 12/1997 | Tarabishy | |
| 5,709,686 A * | 1/1998 | Talos et al. | 606/281 |
| 6,183,472 B1 * | 2/2001 | Lutz | 606/86 A |
| 6,206,881 B1 * | 3/2001 | Frigg et al. | 606/291 |
| 6,306,140 B1 * | 10/2001 | Siddiqui | 606/315 |
| 6,322,562 B1 | 11/2001 | Wolter | |
| 6,342,055 B1 * | 1/2002 | Eisermann et al. | 623/17.16 |
| 6,361,537 B1 * | 3/2002 | Anderson | 606/86 B |
| 6,454,769 B2 * | 9/2002 | Wagner et al. | 606/279 |
| 6,592,586 B1 | 7/2003 | Michelson | |
| 6,701,812 B1 * | 3/2004 | Sawamura | 81/453 |
| 6,827,722 B1 | 12/2004 | Schoenefeld | |
| 6,860,889 B2 | 3/2005 | Bonati et al. | |
| 6,955,677 B2 * | 10/2005 | Dahners | 606/287 |
| 6,981,974 B2 * | 1/2006 | Berger | 606/304 |
| 6,997,086 B1 | 2/2006 | Graham | |
| 7,527,639 B2 * | 5/2009 | Orbay et al. | 606/287 |
| 7,780,711 B2 | 8/2010 | Orbay et al. | |
| 2003/0120277 A1 | 6/2003 | Berger | |
| 2004/0073218 A1 * | 4/2004 | Dahners | 606/69 |
| 2004/0158258 A1 | 8/2004 | Bonati et al. | |
| 2004/0260291 A1 | 12/2004 | Jensen | |
| 2005/0149031 A1 | 7/2005 | Ciccone et al. | |
| 2005/0165400 A1 * | 7/2005 | Fernandez | 606/69 |
| 2005/0222575 A1 | 10/2005 | Ciccone et al. | |
| 2006/0009771 A1 | 1/2006 | Orbay et al. | |
| 2006/0100626 A1 | 5/2006 | Rathbun et al. | |
| 2007/0162018 A1 * | 7/2007 | Jensen et al. | 606/69 |
| 2008/0234677 A1 | 9/2008 | Dahners | |
| 2008/0234749 A1 * | 9/2008 | Forstein | 606/291 |
| 2008/0234752 A1 | 9/2008 | Dahners | |

FOREIGN PATENT DOCUMENTS

| | | |
|---|---|---|
| CN | 2010/072800361660 | 8/2010 |
| CN | 2008800171633 | 12/2012 |
| DE | 4343117 A1 | 6/1995 |
| DE | 19629011 A1 | 1/1998 |
| DE | 19858889 | 6/2000 |
| EP | 0530585 | 3/1993 |
| EP | 1 741 397 | 1/2007 |
| FR | 2 876 270 | 4/2006 |
| WO | WO 2006/037898 | 4/2006 |
| WO | WO 2006/124987 | 11/2006 |
| WO | WO 2006/124987 A1 | 11/2006 |
| WO | WO 2006124987 A1 * | 11/2006 |

OTHER PUBLICATIONS

International Search Report and Written Opinion dated Oct. 6, 2008.
Non-Final Office Action dated, Jun. 23, 2009, for U.S. Appl. No. 11/818,057.
Final Office Action dated Jan. 25, 2010 for U.S. Appl. No. 11/818,057.
Office Action for Japanese Application No. 2009-554517 dated Oct. 16, 2012.
Examination Report for Australian Application Serial No. AU 2008227127 dated Jul. 24, 2012.
European Patent Office Notice of Publication for EP 08725277.1 dated Dec. 16, 2009.
Advisory Action dated Jun. 10, 2010 for U.S. Appl. No. 11/818,057.
International Preliminary Report on Patentability for PCT/US2008/007259 dated Dec. 17, 2009.
First Office Action for Chinese Application No. 200880017163.3 dated Mar. 15, 2011.
Notification to Grant for Chinese Application No. CN 2008/80017163 dated Aug. 3, 2012.
Extended European Search Report for Application Serial No. EP 08 72 5277 dated Jul. 2, 2012.
Second Office Action for Chinese Application No. 200880017163.3 dated Apr. 1, 2012.
Israeli Office Action for IL Application No. 201056 dated Apr. 30, 2012.
European Office Action for Application No. 08 725 277.1-1506 dated Mar. 7, 2013.
Wolter et al., "Universal Internal Titanium Fixation Device: Developmental History, Principle, Mechanics, Implant Design and Surgical Use," Trauma and Occupational Disorders (1999) (English translation).
Webster's II New Riverside Dictionary (1996) (definitions of "protrusion" and "interstice").
Inter Partes Review for *Smith & Nephew Inc.* vs. *The University of North Carolina at Chapel Hill* (Case No. IPR2014-00112—US 6,955,677) filed Oct. 31, 2013.
Inter Partes Review for *Wright Medical Technology, Inc.* vs. *The University of North Carolina at Chapel Hill* (Case No. To be assigned—Re: US,6,955,677) filed Apr. 14, 2014.
Office Action with Restriction Requirement for U.S. Appl. No. 11/818,057 dated Nov. 25, 2013.
Israeli Office Action for IL Application No. 201056 dated Dec. 18, 2013.
Notice of Allowance for U.S. Appl. No. 11/818,057.

* cited by examiner

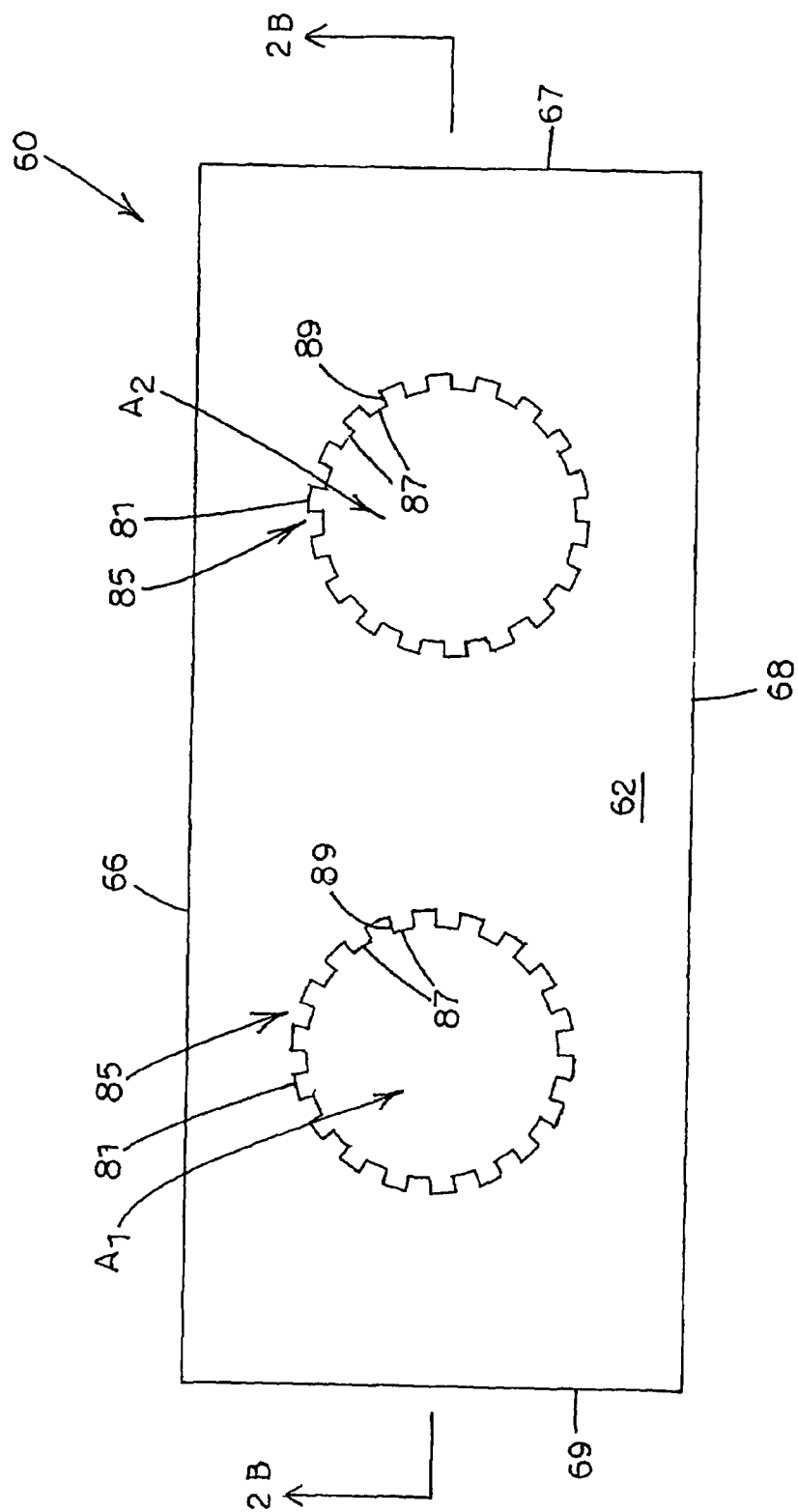

ANTI-UNSCREWING AND MULTI-ANGULAR FASTENING APPARATUSES AND METHODS FOR SURGICAL BONE SCREW/PLATE SYSTEMS

TECHNICAL FIELD

The present disclosure relates generally to the design of fasteners and components to which fasteners are affixed. A specific application of the present disclosure relates to the design and use of bone screw/plate systems in the course of orthopaedic surgical procedures.

BACKGROUND

A variety of techniques exist in the field of orthopaedic surgery for treating bone fractures. Many known techniques utilize bone screws and bone fixation plates. Typically, the plate is used to stabilize the site of a bone fracture, and one or more bone screws are inserted through apertures of the plate and threaded into the bone material so as to secure the plate to the bone material. It is also known that bone screw/plate systems can be improved by machining a thread onto the head of the bone screw, in addition to the thread normally machined onto the main shaft of the screw. In connection with the use of threaded-head screws, the apertures of the plate are threaded to matingly receive the threads of the screw head. Thus, as the screw is inserted into an aperture of the plate and threaded into the bone material, the head of the screw likewise is threaded into the aperture. As a result, the screw becomes rigidly affixed to the plate, in effect locking to the plate rather than simply bearing against the plate. Examples of threaded-head bone screws and threaded-aperture bone plates are disclosed in U.S. Pat. No. 5,709,686 to Talus et al.: U.S. Pat. No. 6,206,881 to Frigg et al.: and U.S. Pat. No. 6,306,140 to Siddigui.

The use of threaded-head screws and threaded-aperture plates provides certain advantages. It is known that some types of small bone fragments tend to change position relative to the plate over time. This deleterious condition can result from the "toggling" of the screws affixed to the plate. However, when multiple screws are rigidly fixed to the plate by mating the respective threads of the screw heads with the threads of the corresponding plate apertures, the screws do not toggle in the plate. The locking action provided by the threaded-head screw in combination with the threaded-aperture plate prevents motion between the bone fragment and the plate as well as premature loosening of the screws.

Although the use of threaded-head screws has provided improvements in orthopaedic surgical techniques, there remains the disadvantage that these screw/plate systems are unidirectional. That is, the thread formed on the inside surface of the aperture of the plate is structurally fixed at a constant helical angle with respect to the central axis passing through the center point of the aperture. Hence, the head of a conventional threaded-head screw can only be rigidly affixed to the plate by mating its thread with that of the aperture, such that the bone screw is always inserted and threaded in one direction, e.g., perpendicularly or coaxially with respect to the plate.

Recent developments in this field provide screw/plate systems that allow the surgeon to choose the angle at which the screw is inserted through, and rigidly affixed in, an aperture of the plate. Examples of such systems are disclosed in U.S. Pat. No. 6,955,677 to Dahners. Such improvements enable the surgeon to direct the bone screw toward bone fragments that are not situated directly beneath the aperture of the plate, and also provide flexibility in the placement of the plate in relation to the bone fracture. These systems, however, do not address the possibility of the screws unscrewing or backing out of the plate due to common loading and unloading associated with this application. This is problematic if it should occur since the plate becomes loose and fails to perform its intended function properly. Furthermore, in anatomically critical areas, such as the anterior cervical spine, impingement of the backed-out screw on overlying structures can even cause significant morbidity and mortality.

Also, current screw driver-like driver tools for inserting fasteners such as screws are limiting in that angular placement is difficult due to the tendency of the screws to fall off the driver tool when placed in an angular orientation.

It would therefore be advantageous to provide a further improved screw/plate system that prevents the screw from backing out of the plate regardless of whether the screw is in a coaxial or non-coaxial position relative to the aperture in the plate. Although the screw cannot back-out of the plate, the system can further include a driving tool that permits the surgeon to secure and remove the screw if necessary in order to remove and recontour or resituate the plate, to adjust the screw angle if the initial insertion proves unsatisfactory, or to remove the plate after fracture healing. Thus, the further improved system provides anti-unscrewing capabilities, while at the same time offering selective removability. Furthermore, a driver tool is provided that can facilitate use of such a system and can provide improved angular adjustability and control for inserting screws at various angles to the central axis of an aperture in the plate.

SUMMARY

The present disclosure in broad terms provides an improved multi-angular fastening bone screw/plate system that comprises a plate or other component suitable for affixation by a fastener that will not back-out of the plate. The plate has one or more apertures through which one or more corresponding fasteners can be inserted. Notably absent from these apertures are any forms of permanent internal thread structures as found in the prior art and which, as indicated above, can be a limitation in applications such as the treatment of bone trauma. Each aperture is bounded by a region structured to enable the fastener, and particularly a threaded head portion of the fastener, to be tapped into the material constituting the region. By providing this tappable region, the fastener can be inserted at any desired angle in relation to the central axis of the aperture, thereby providing significant flexibility in practice. The fastener is designed to include notches or slots that engage the tappable region in an anti-unscrewing manner to prevent the fastener from backing out of the plate. The bone screw/plate also provides a tool that permits removal of a fastener which employs the anti-unscrewing technology.

While it is contemplated that the disclosure can be applied in a wide range of fastening and fixation techniques, particular advantage is found in the field of orthopaedic surgery. Embodiments of the disclosure can be practiced in any surgical procedure that conventionally involves the use of bone screw/plate systems. Examples include the treatment of general bone trauma, stabilization of metaphyseal fractures, treatment of osteoporotic bones, bone fusion, joint prosthesis, spinal alignment or correction, and the like.

According to one embodiment of the present disclosure, a surgical plate adapted for fixation with a bone screw is provided. The plate comprises first and second opposing major surfaces, and an inside surface extending between the first and second major surfaces. The inside surface defines an aperture that is generally coaxially disposed about an aperture axis. A non-threaded tappable contact region is disposed on the inside surface of the aperture. The tappable contact region has a minimum inside diameter that is large enough to permit a bone screw having at least one slot to pass therethrough at an insertion angle defined between a longitudinal axis of the fastener and the aperture axis. The tappable contact region is adapted for being tapped by an external thread of the bone screw to affix the bone screw to the tappable contact region at the insertion angle. The tappable contact region is further adapted to engage the at least one slot of the fastener to prevent backing out of the fastener from the aperture of the plate.

According to one aspect of this embodiment, the fastener has at least one slot for permanently affixing the fastener to the plate. According to another aspect, the fastener has a plurality of slots that facilitate removal of the anti-unscrewing fastener from the plate.

According to a further aspect of this embodiment, a fastener driver comprises slot engagement portions for deflecting protrusions of the tappable contact region from within the slots to permit removal of the fastener from the plate. According to yet another aspect, the fastener driver comprises a nipple to provide improved angular insertion of the fastener. According to a yet further aspect, the fastener driver defines a shaft that receives a driver rod for facilitating angular insertion of the fastener. According to a further embodiment, an angular insertion tool is provided to enable rigid control of the fastener while on the end of the tool to promote insertion of the fastener at a precise angle.

It is therefore an object of the present disclosure to provide anti-unscrewing devices and methods for preventing backing out of a fastener from a bone screw/plate system, while also providing a tool that permits selective removal of the fastener such that the anti-unscrewing feature is not permanent.

An object having been stated hereinabove, and which is achieved in whole or in part by the subject matter disclosed herein, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures in which:

FIG. 2A is a top plan view of a fastener receiving member provided in accordance with the present disclosure;

DETAILED DESCRIPTION

Reference will now be made in detail to presently preferred embodiments of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Figure 1:
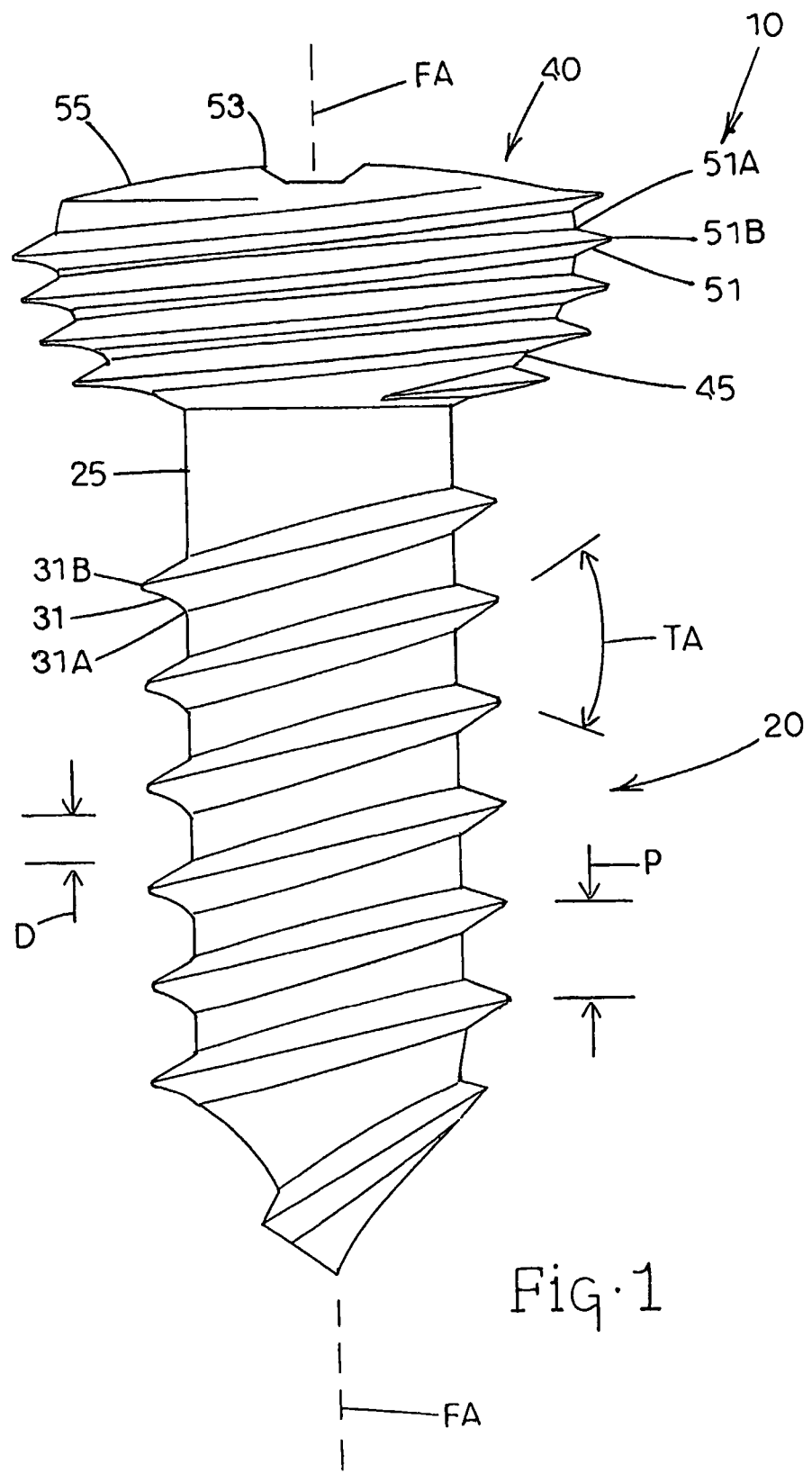
FIG. 1 is an elevation view of a fastener provided in accordance with the present disclosure.

Referring now to FIG. 1, one example of a threaded-head fastener, generally designated 10, is illustrated in accordance with the present disclosure. Fastener 10 can be constructed from any material appropriate for withstanding compressive, tensile, torque, or other forces encountered during and after application of fastener 10 to a target site. In the context of orthopaedic surgery, fastener 10 is preferably constructed from a biocompatible metal or metal alloy such as stainless steel, titanium, chromium, or alloys thereof. As is appreciated by persons skilled in the art, fastener 10 could also be constructed from a suitable ceramic material or a polymeric material such as a resorbable polymer, or could be coated with a polymeric film. Fastener 10 comprises an elongate section, generally designated 20, and an adjoining head section, generally designated 40, both of which are generally arranged along a longitudinal fastener axis FA. Elongate section 20 comprises a shaft having a first outer surface 25 coaxially disposed in relation to fastener axis FA. Preferably, first outer surface 25 is cylindrical. Elongate section 20 is machined to form a first thread 31 thereon. First thread 31 has a root 31A adjoining first outer surface 25 from which first thread 31 extends generally radially outwardly to terminate at a crest 31B. First thread 31 winds around first outer surface 25 or a length thereof in a generally helical fashion. In the illustrated example, first thread 31 has a conical or "V" cross-sectional profile and thus tapers from first outer surface 25 to its crest 31B.

In a one embodiment of the disclosure in which fastener 10 is utilized as a bone screw for anchoring to bone material B such as a bone fragment, the illustrated "V" profile of first thread 31 is advantageous in that renders fastener 10 self-tapping. The present disclosure, however, is not limited to any particular design for first thread 31. For instance, the profile of first thread 31 could be rectilinear or square, with its crest 31B being a generally flat surface. Alternatively, the profile of first thread 31 could be trapezoidal (i.e., an "Acme" thread). The degree of sharpness or flatness of crest 31B is not limited, and crest 31B could be rounded. Moreover, the present disclosure is not limited to any particular diameter of first outer surface 25, diameter of crest 31B, thread angle TA between the side walls of adjacent thread passes, or thread pitch P (i.e., the axial distance between the crest portions of adjacent thread passes, or the reciprocal of the number of thread passes per inch). Additionally, first thread 31 could be a multiple-threaded or multi-start design, in which two or more individual threads are cut beside each other. First thread 31 could also constitute one or more single threads formed on different axial sections of shaft. Also, pitch P of first thread 31 could be such that adjacent thread passes are separated from each other by an axial distance D over which only first outer surface 25 of shaft exists. Finally, the "hand" or "sense" associated with the turning of first thread 31 about fastener axis FA may or may not follow the standard right-hand rule.

Figure 4:
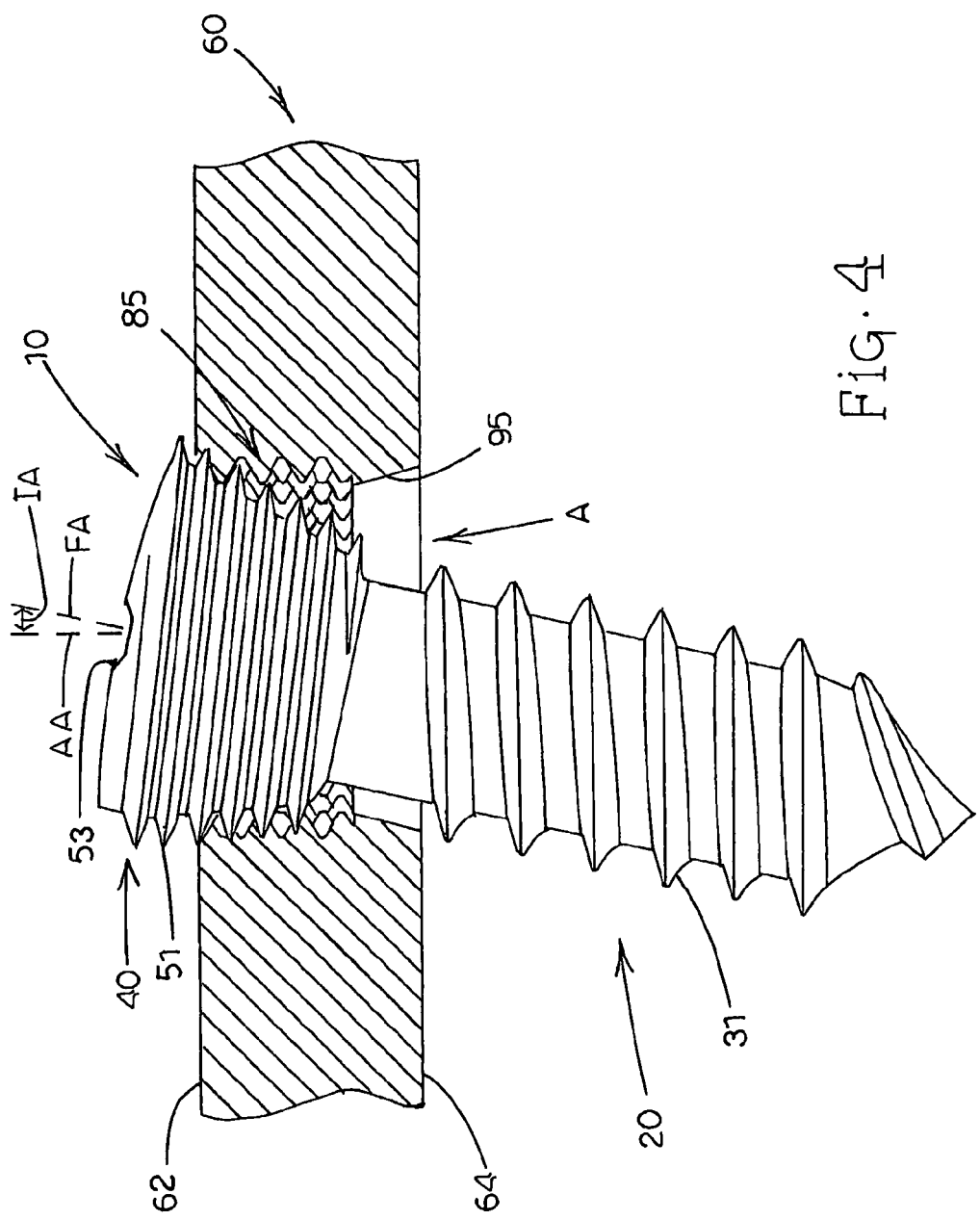
FIG. 4 is a partially cut away and vertical cross-sectional view of a fastener and fastener receiving member according to an alternative embodiment of the present disclosure.
Figure 5:
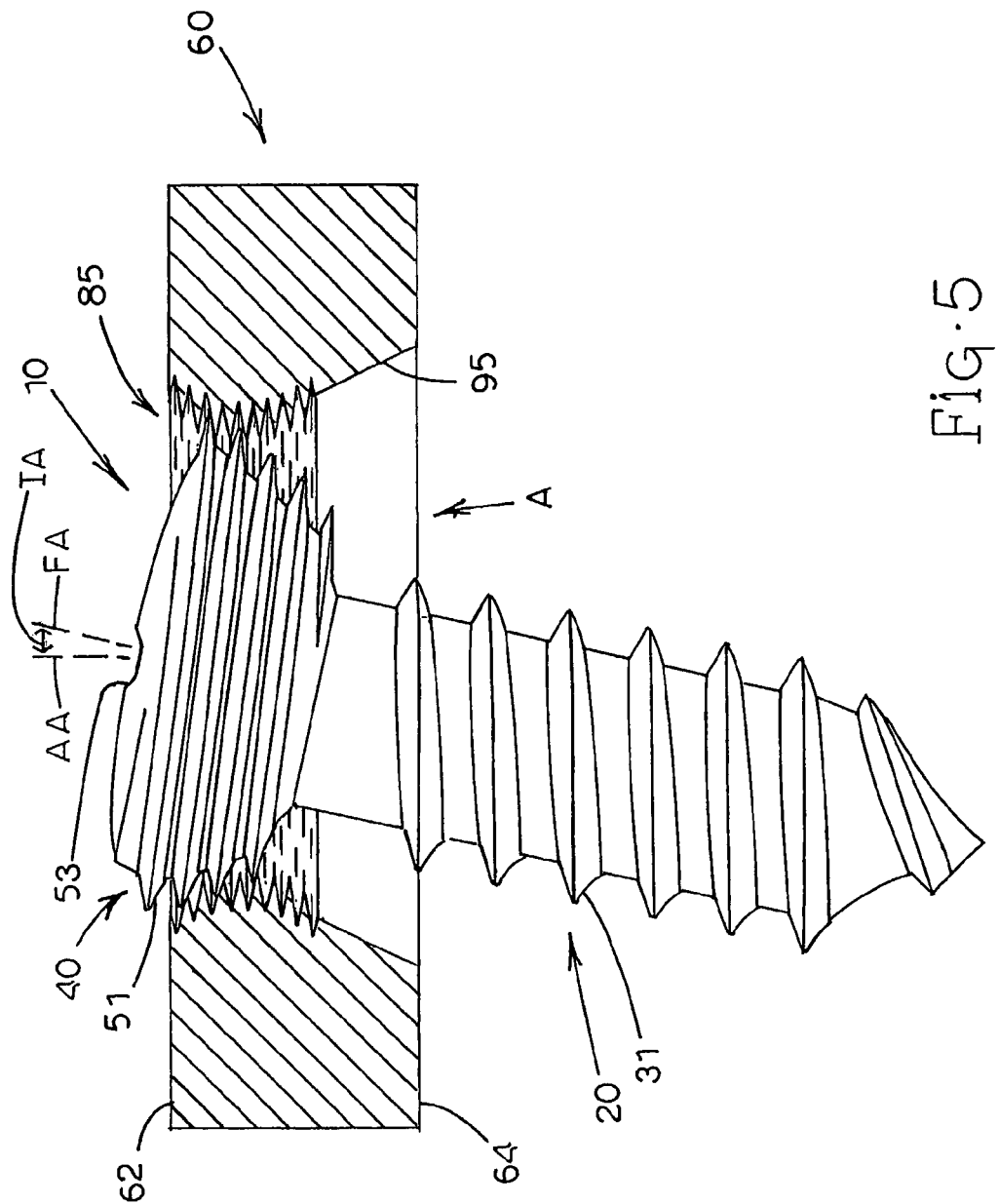
FIG. 5 is a partially cut away and vertical cross-sectional view of a fastener and fastener receiving member according to another alternative embodiment of the present disclosure.

With continuing reference to FIG. 1, head section 40 comprises a second outer surface 45 coaxially disposed in relation to fastener axis FA. In the example illustrated in FIG. 1, the shape of head section 40, i.e., the cross-sectional profile of second outer surface 45, is substantially hemispherical or parabolic. It will be understood, however, that head section 40 can have other types of rounded shapes, and its profile can be either convex or concave. Moreover, the shape of head section 40 can be substantially frusto-conical as shown in FIGS. 4 and 5. In addition, the shape of head section 40 can be a composite form, such as a converging/diverging or "trumpet-shaped" profile. Head section 40 is machined to form a second thread 51 thereon. Second thread 51 has a root adjoining second outer surface 45 from which second thread 51 extends generally radially outwardly to terminate at a crest 51B. Second thread 51 winds around second outer surface 45 in a generally helical fashion. To facilitate the turning of fastener 10 by the user thereof, a recess 53 is formed in a top surface 55 of head section 40 for the insertion of an appropriate tool such as a screwdriver, key, or wrench. The shape of recess 53 can be a single or cross-shaped slot, a square, a hexagon, a star, or the like.

In the illustrated example, second thread 51 has a conical or "V" profile and thus tapers from second outer surface 45 to crest 51B. The "V" profile of second thread 51 is preferred because it facilitates the self-tapping of head section 40 into a plate or other fastener receiving member 60 (see, e.g., FIGS. 2A and 2B), in accordance with the present disclosure and as described below. However, like first thread 31 of elongate section 20, the present disclosure is not limited to any particular design for second thread 51. Thus, no limitations are made with regard to the profile or shape of first thread 31, the degree of sharpness or flatness of its crest 31B, the outer diameter of any portion of second outer surface 45 or crest 31B (although the average diameter of head section 40 is greater than that of elongate section 20), the thread angle TA, the thread pitch P, the number and locations of the threads constituting second thread 51, or the turning direction of second thread 51 with respect to fastener axis FA.

In an alternative embodiment, elongate section 20 is not threaded, and fastener 10 takes the form of a peg or a pin. This alternative embodiment may be preferred in certain procedures where, for instance, the main object is to prevent tilting of a bone segment, as well as other procedures where there is no concern of fastener 10 pulling out from the bone and hence no need for elongate section 20 to be threaded. In these implementations, head section 40 is threaded, and thus the advantages and benefits of the present disclosure as described herein apply.

Turning to FIGS. 2A-2D, a fastener receiving member, generally designated 60, is illustrated in accordance with the present disclosure. In the illustrated example, fastener receiving member 60 is provided in the form of a mounting plate, such as a bone plate for use in orthopaedic surgical procedures. Fastener receiving member 60 can be constructed from any material appropriate for withstanding compressive, tensile, torque, or other forces encountered during and after application of fastener 10 to fastener receiving member 60 at a target site. In the context of orthopaedic surgery, fastener receiving member 60 is preferably constructed from a biocompatible metal or metal alloy such as stainless steel, titanium, cobalt, chromium, tungsten, tantalum, molybdenum, gold, and alloys thereof. Alternatively, fastener receiving member 60 can be constructed from a suitable ceramic or polymeric material. The polymeric material may be reinforced with glass, carbon, or metal fibers.

Fastener receiving member 60 comprises a first major outer surface 62, an opposing second major outer surface 64, and outer lateral edges 66, 67, 68 and 69 at the perimeter. In orthopaedic applications, second outer surface 64 can in some cases be used for contact with bone material B (see FIG. 3), while in other cases actual contact is unnecessary or undesirable. While in the illustrated example first and second outer surfaces 62 and 64 are planar, it will be understood that the cross-section of fastener receiving member 60 or certain portions thereof can have a contoured profile. For instance, in some types of orthopaedic applications, minimum contact between fastener receiving member 60 and the target bone material B might be desired. In such a case, second outer surface 64 or a portion thereof can be convex.

One or more apertures, generally designated A (e.g., apertures $A_1$ and $A_2$ shown in FIGS. 2A and 2B), are formed through the thickness of fastener receiving member 60 for receiving one or more elongate sections 20 of corresponding fasteners 10 therethrough. Each aperture A is defined by an inside surface 81 cut through the thickness of fastener receiving member 60. Each aperture A is generally transversely oriented in relation to first and second outer surfaces 62 and 64, and thus is generally coaxially disposed about a central aperture axis AA (e.g., aperture axis $AA_1$ or $AA_2$ shown in FIG. 2B) directed through the thickness of fastener receiving member 60. The precise number and arrangement of such apertures A can depend on the intended use for fastener receiving member 60. It will be understood, however, that the present disclosure contemplates procedures in which a multi-apertured fastener receiving member 60 is employed in connection with a single fastener 10, with one aperture A of such fastener receiving member 60 being selected by the user for interfacing with the single fastener 10.

Figure 3:
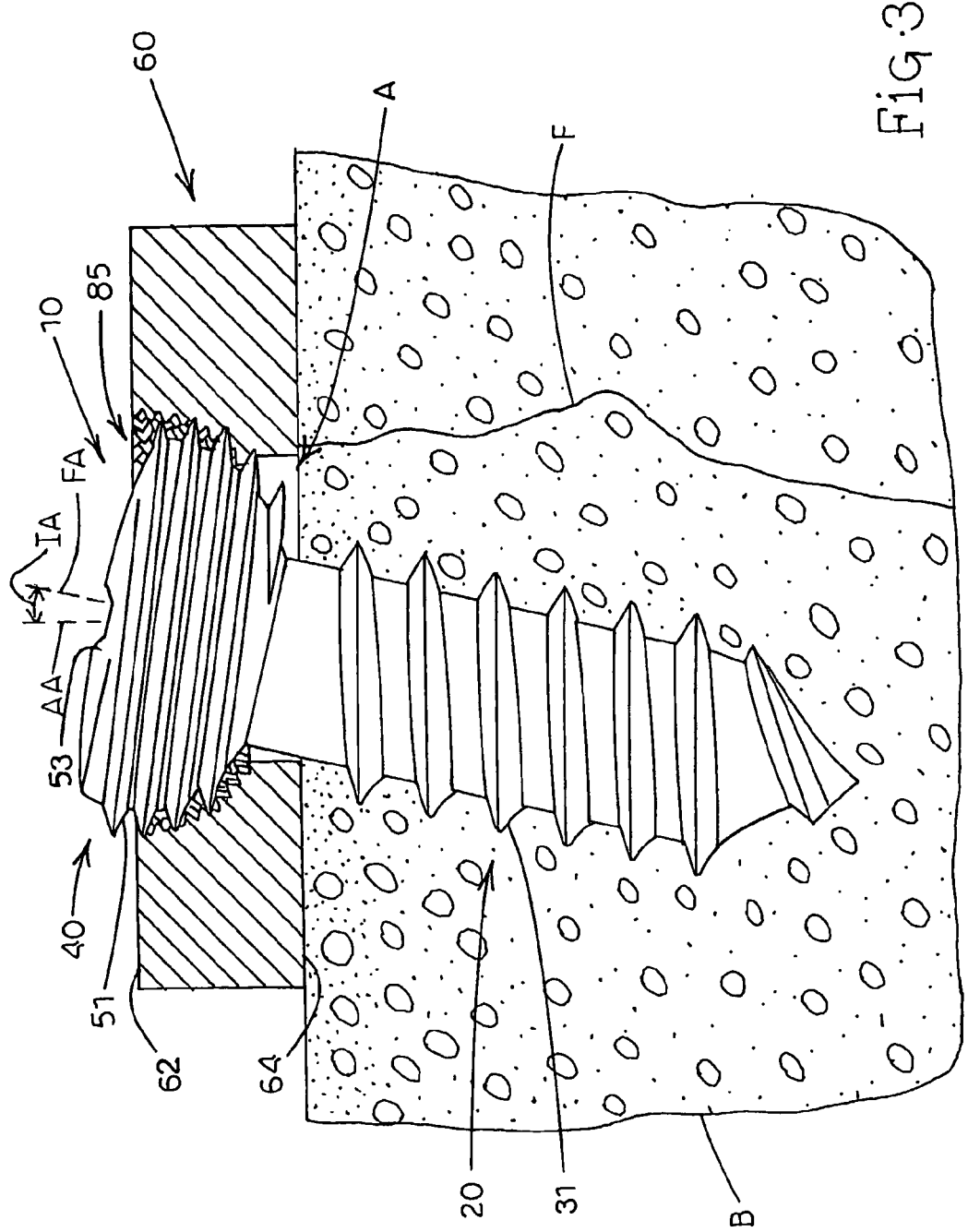
FIG. 3 is a partially cut away and vertical cross-sectional view illustrating an application of the present disclosure in which the fastener is affixed to the fastener receiving member and anchored to an object such as bone material at a desired insertion angle.

As indicated above, the present disclosure departs from the conventional use of a thread formed on inside surface 81 of aperture A for mating with the thread of a screw head. That is, apertures A of fastener receiving member 60 do not contain a permanent helical thread structure of fixed orientation. Instead, a tappable contact region, generally designated 85, is disposed on each inside surface 81 of fastener receiving member 60. The term "tappable" is used herein to denote that contact region 85 is structured such that it can be tapped by second thread 51 of head section 40 of fastener 10 in response to forceful insertion and rotation of head section 40 into the material of contact region 85. As described below in connection with FIG. 3, this enables the user to manipulate second thread 51 of head section 40 to form, in effect, a custom internal thread in contact region 85 sufficient to maintain fastener 10 at an arbitrary orientation in relation to receiving member 60 selected by the user. In FIG. 3, this orientation is represented by an insertion angle IA, defined between fastener axis FA and aperture axis AA. In accordance with the present disclosure, insertion angle IA can range from 0 to 90 degrees wherein at 0 degrees fastener axis FA coincides with aperture axis AA. Due to the relative positions of aperture A, second outer surface 64 and fastener 10, insertion angle IA in practice will be less than 90 degrees.

Figure 2B:
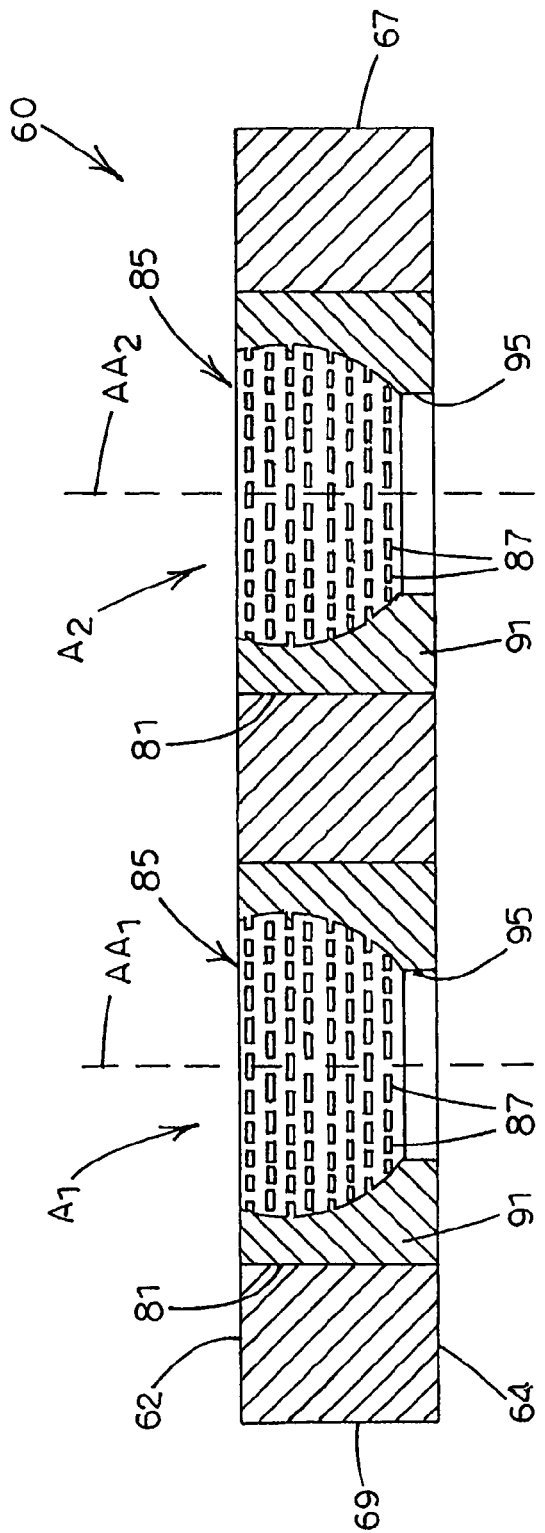
FIG. 2B is a vertical cross-sectional side view of the fastener receiving member illustrated in FIG. 2A taken along cut-away line 2B-2B in FIG. 2A.

In the embodiment illustrated in FIGS. 2A-2D, the tappable property is realized by structuring contact region 85 as a matrix of protrusions 87 and interstices 89 between protrusions 87. Protrusions 87 can be provided in any protruding form, such as pegs, bristles or tines. Protrusions 87 are based on inside surface 81 and extend generally radially inwardly into the open space of apertures A. Protrusions 87 can be formed directly from inside surface 81 and the region of fastener receiving member 60 circumscribing aperture A. Alternatively, as shown in FIG. 2B, protrusions 87 can be formed on a substrate 91 (see FIG. 2B) that is thereafter fitted to inside surface 81 as an insert, such as by press-fitting or binding. The material selected for protrusions 87 can be any material suitable for tapping by fastener 10. Non-limiting examples include stainless steel, titanium, cobalt, chromium, tungsten, tantalum, molybdenum, gold, and alloys thereof, as well as suitable polymers.

It will be noted that the density of protrusions 87 over the area of inside surface 81, and the size of individual protrusions 87, are not limited by the present disclosure, so long as the matrix formed on inside surface 81 renders contact region 85 tappable. Accordingly, the matrix of protrusions 87 can appear as a bristle board or a porous surface. The characteristic cross-sectional dimension of each protrusion 87 (e.g., diameter, width, or the like) can range from approximately 1 micron to approximately 25 mm, although the present disclosure is not limited to this range. The density of protrusions 87 over the area of inside surface 81 from which they protrude can range from approximately 5 to approximately 65%, although the present disclosure is not limited to this range. Protrusions 87 can be formed by any suitable means, such as growing protrusions 87 by material deposition, forming protrusions 87 by coating, welding protrusions 87 to inside surface 81, or forming ridges or grooves and subsequently cutting transversely through the ridges to discretize the ridges into protrusions 87.

Figure 2D:
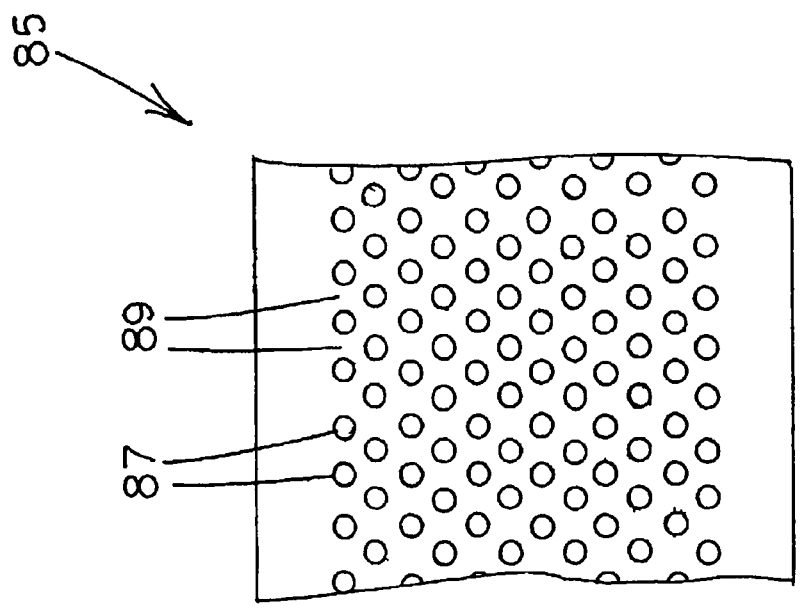
FIG. 2D is a plan view of a section of a contact region in accordance with another embodiment of the present disclosure.
Figure 2C:
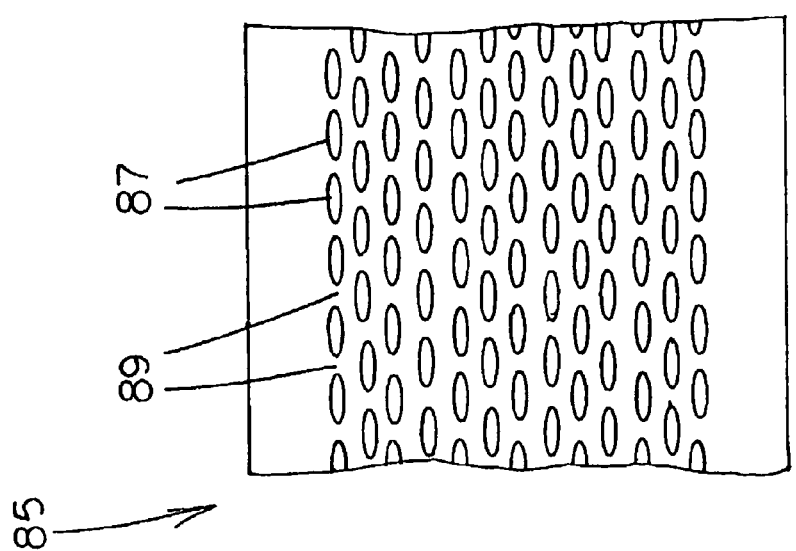
FIG. 2C is a plan view of a section of a contact region provided with the fastener receiving member in accordance with one embodiment of the present disclosure.

It will be further noted that in the embodiment illustrated in FIGS. 2A and 2B, each protrusion 87 has a generally rectilinear cross-section. The present disclosure, however, encompasses within its scope any cross-section suitable for realizing the tappable property of contact region 85. Hence, as another example, FIG. 2C illustrates an area of contact region 85 in which protrusions 87 are generally elliptical in cross-section. As a further example, FIG. 2D illustrates an area of contact region in which protrusions 87 are generally circular in cross-section. In addition, depending on the density and size of protrusions 87 and the pattern defined by the matrix, protrusions 87 may or may not be deformable as necessary to realize the tappable property of contact region 85.

As seen from the perspective of FIG. 2B, the resultant profile of contact region 85 is illustrated in one embodiment as being rounded to accommodate the rounded profile of head section 40 of fastener 10. The term "resultant" is meant to denote that the profile can be defined by the inside surface 81 itself with each protrusion 87 having a substantially uniform length, or alternatively, the profile can be defined by protrusions 87 of varying lengths. The present disclosure, however, is not limited to any specific profile for contact region 85. In addition, in some embodiments of the present disclosure, contact region 85 is not formed over the entire axial length of inside surface 81. Thus, in FIG. 2B, contact region 85 terminates at a lower section 95 of inside surface 81 (or substrate 91) proximate to second outer surface 64 of fastener receiving member 60.

While the profile of lower section 95 in FIG. 2A is cylindrical, other profiles for lower section 95 are suitable in accordance with the present disclosure. The respective profiles for contact region 85 and any exposed portion of inside surface 81 such as lower section 95 will be dictated in part by the shape of head section 40 of fastener 10, and also by the need to affix fastener 10 over a wide range of available insertion angles IA in relation to receiving member 60 and/or the bone material B or other object in which fastener 10 is to be anchored. Thus, in FIG. 4, a fastener 10 with a conical head section 40 is employed in connection with a receiving member 60 having a contact region 85 of cylindrical profile and a lower section 95 that tapers from second outer surface 64 to contact region 85. As another example, in FIG. 5, a fastener 10 with a rounded head section 40 is employed in connection with a receiving member 60 having a contact region 85 of converging/diverging or trumpet-shaped profile and a lower section 95 of tapering profile. It will be noted for all embodiments that the minimum inside diameter of contact region 85 should be large enough to provide clearance for elongate section 20 and its first thread 31 to pass through aperture A. As one example, the minimum inside diameter can range from approximately 0.5 to approximately 10 mm. In non-orthopaedic applications, the minimum inside diameter can be greater than 10 mm.

Figure 6:
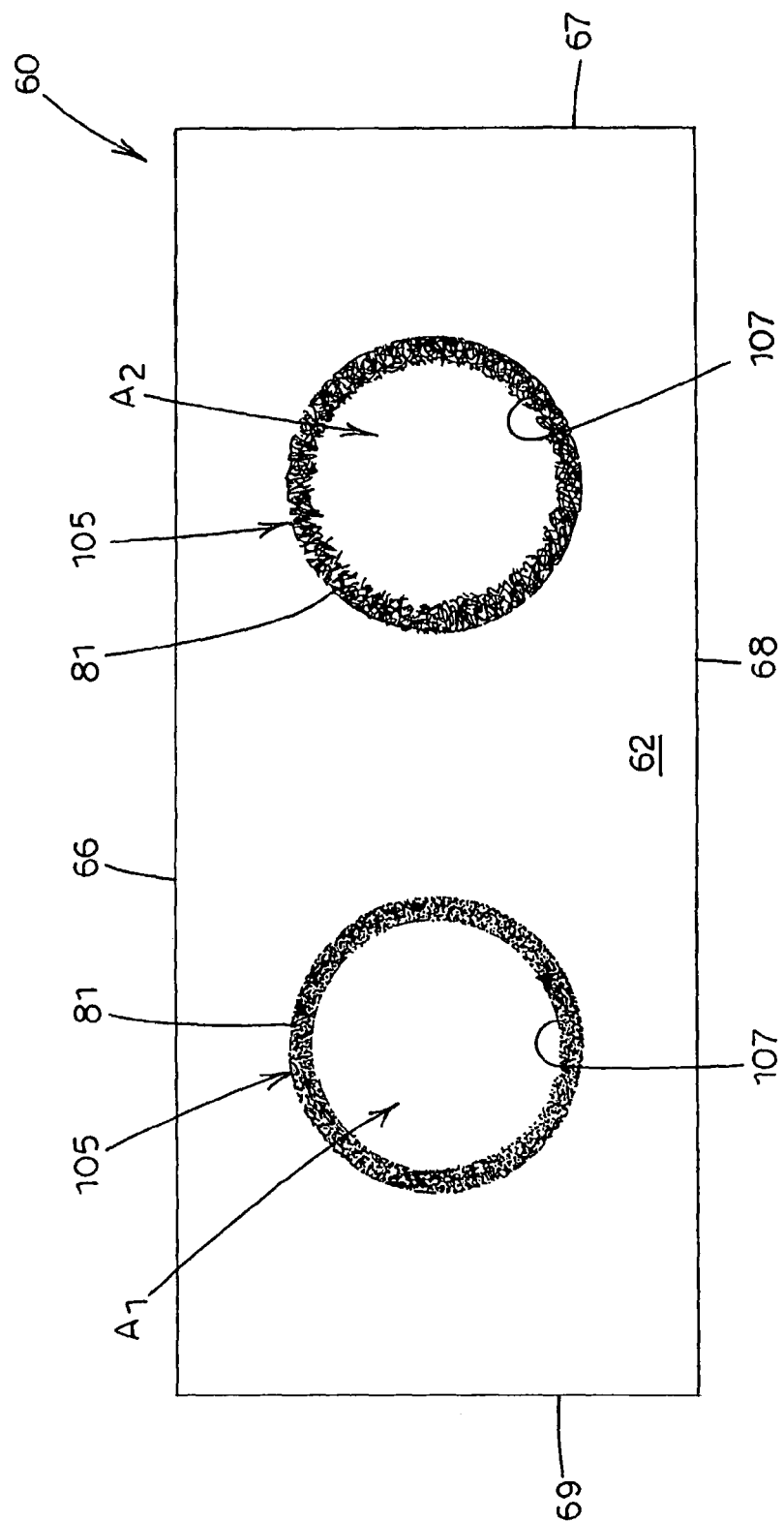
FIG. 6 is a top plan view of a fastener receiving member provided with an alternative contact region provided in accordance with the present disclosure.
Figure 7:
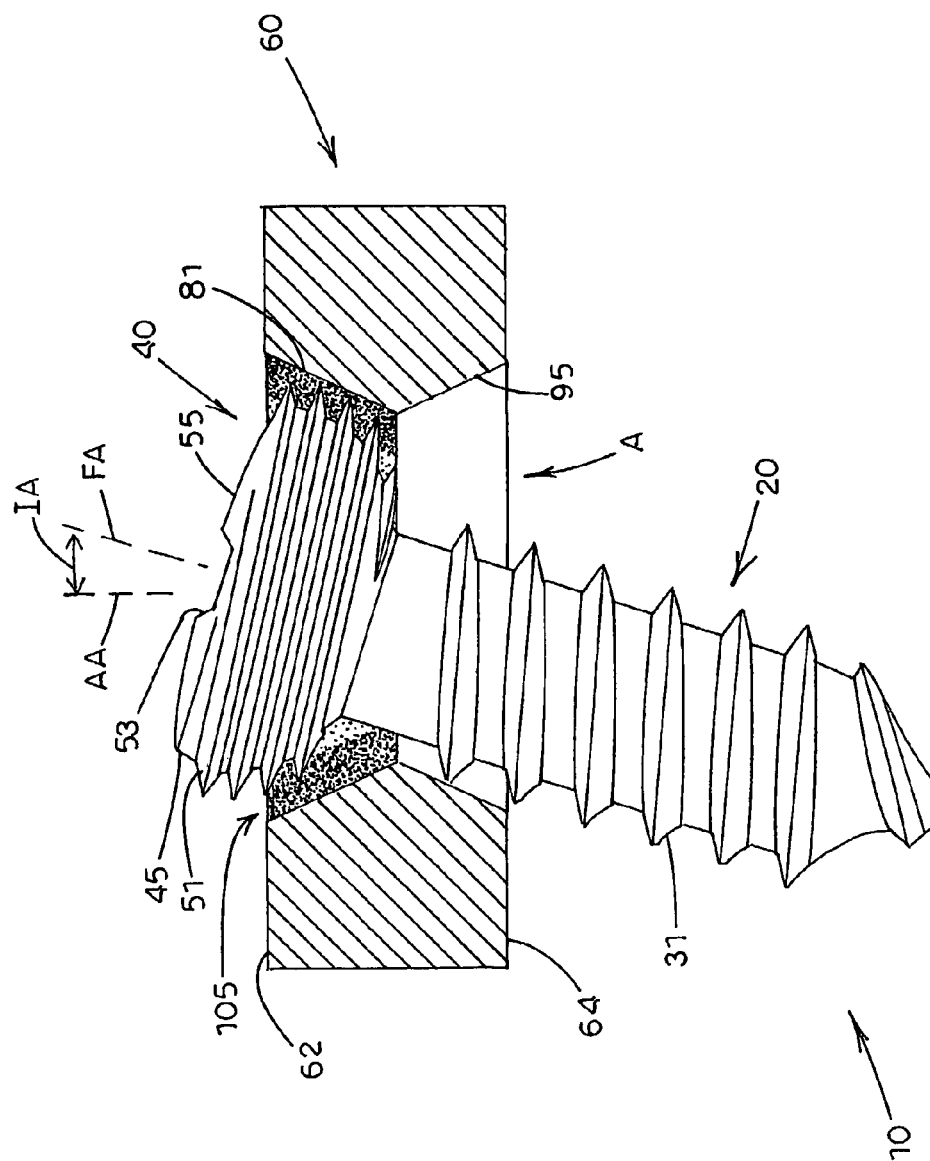
FIG. 7 is a partially cut away and vertical cross-sectional view illustrating the fastener affixed to the fastener receiving member illustrated in FIG. 6.

Referring now to FIGS. 6 and 7, an alternative embodiment of a tappable contact region, generally designated 105, is illustrated. In this embodiment, tappable contact region 105 takes the form of a matrix or mesh of fiber metal 107 that lines inside surface 81 of each aperture A of fastener receiving member 60. As understood by persons skilled in the art, fiber metal consists of a porous or interstitial aggregate of metal or metal alloy wires or fibers. The characteristic cross-sectional dimension of each fiber (e.g., diameter, width, or the like) can range from approximately 1 micron to approximately 25 mm. The porosity of the matrix can range from approximately 40 to approximately 90%. The fibers are often interlocked and kinked in any number of different patterns, and often has the appearance of steel wool. The aggregate can be formed by a variety of techniques. As one example, the fibers can be molded and sintered so as create metallurgical bonds between the fibers and a base surface. The composition of the fibers of contact region 105 can be any biocompatible material that provides contact region 105 with mechanical strength and deformability suitable for being tapped by fastener 10 in accordance with the present disclosure. Non-limiting examples include stainless steel, titanium, cobalt, chromium, tungsten, tantalum, molybdenum, gold, and alloys thereof.

An example of a method for affixing fastener 10 to fastener receiving member 60 will now be described by referring back to FIG. 3, with the understanding that the method can likewise be described in association with the other embodiments illustrated in FIGS. 4-7. It will be further understood that while the present example is given in the context of an orthopaedic surgical procedure, the present disclosure is not so limited. That is, the fastener/receiver system provided by the present disclosure can be applied to any procedure, surgical or non-surgical, in which a threaded fastener is to be tapped into an object and which would benefit by the ability to rigidly orient such fastener at a desired angle in relation to a mounting structure such as fastener receiving member 60.

Turning now to FIG. 3, the surgeon accesses the surgical site of interest, which can be, for example, an internal site at which a bone fracture F is located and requires stabilization to ensure proper healing. The surgeon mounts fastener receiving member 60 against bone material B at a desired location thereof in relation to the bone fracture F. A suitable alignment or mounting tool (not shown) can be employed to retain receiving member 60 in the desired position prior to complete affixation of fastener 10. The surgeon then selects an insertion angle IA, defined hereinabove, as the direction along which fastener 10 is to be inserted through a selected aperture A of receiving member 60 and subsequently driven into a target section of bone material B. If receiving member 60 includes more than one aperture A, the surgeon also selects the specific aperture A to be used. After selecting insertion angle IA and aperture A, the surgeon inserts elongate section 20 of fastener 10 through aperture A until the tip of elongate section 20 contacts bone material B beneath aperture A. In some cases, at this point a hole might be drilled or tapped into bone material B along insertion angle IA to facilitate the initial tapping by fastener 10. The surgeon then inserts an appropriate driving tool (not shown) into recess 53 of head section 40 of fastener 10, and manipulates the driving tool to rotate fastener 10 while forcefully bearing fastener 10 against bone material B. This causes first thread 31 of elongate section 20 to tap into bone material B and anchor fastener 10 to bone material B. As elongate section 20 is driven further through aperture A and into bone material B, head section 40 eventually encounters contact region 85 of aperture A. Due to the intervening presence of contact region 85, the continued driving of fastener 10 into bone material B at this stage causes second thread 51 of head section 40 to tap into contact region 85, thereby rigidly affixing fastener 10 to receiving member 60 at the desired insertion angle IA.

The manner by which head section 40 of fastener 10 is affixed to aperture A of receiving member 60 depends on whether contact region 85 illustrated in FIGS. 2A-3 or contact region 105 illustrated in FIGS. 6 and 7 is provided. In the use of contact region 85, second thread 51 of head section 40 is driven through a series of available interstices 89 (see, e.g., FIGS. 2C and 2D) and between a series of protrusions 87 adjacent to these interstices 89. The driving of second thread 51 causes this series of protrusions 87 to contact second thread 51 and maintain fastener 10 at the desired insertion angle IA. As described hereinabove, protrusions 87 contacting second thread 51 may or may not deform or otherwise move in response to the driving of second thread 51 into contact region 85. On the other hand, in the use of contact region 105, the metal fibers will deflect in response to the driving of second thread 51 and envelop second thread 51. The mechanical strength of the fibers contacting or proximate to second thread 51 is sufficient to maintain fastener 10 at the desired insertion angle IA. Some of the fibers may be cut in response to the driving of second thread 51 into contact region 105. With the use of either contact region 85 or contact region 105, the driving of second thread 51 through aperture A in effect forms a custom internal thread in contact region 85 or 105 that is complimentary to the orientation and structure of second thread 51 and turns in relation to fastener axis FA.

Depending on the nature of the procedure being executed, the surgeon can affix additional fasteners 10 to additional apertures A of receiving member 60, either at the same insertion angle IA as the illustrated fastener 10 or at different angles. It will be noted that, depending on the number of fasteners 10 utilized and how far each is threaded into its corresponding aperture A, the mechanical strength of the interface between each corresponding second thread 51 and contact region 85 or 105 can be made sufficient to cause compression of receiving member 60 against bone material B if desired by the surgeon.

As an alternative to the embodiments specifically illustrated in FIGS. 1-7, the interface between second thread 51 of head section 40 and contact region 85 or 105 of aperture A could be reversed. That is, head section 40 of fastener 10 could be provided with contact region 85 or 105, and aperture A of fastener receiving member 60 could be provided with second thread 51. This alternative embodiment likewise enables fastener 10 to be rigidly secured non-coaxially to aperture A.

Anti-Unscrewing Embodiments of Multi-Angular Bone Screw/Plate Systems

I. Anti-Unscrewing System

Figure 8:
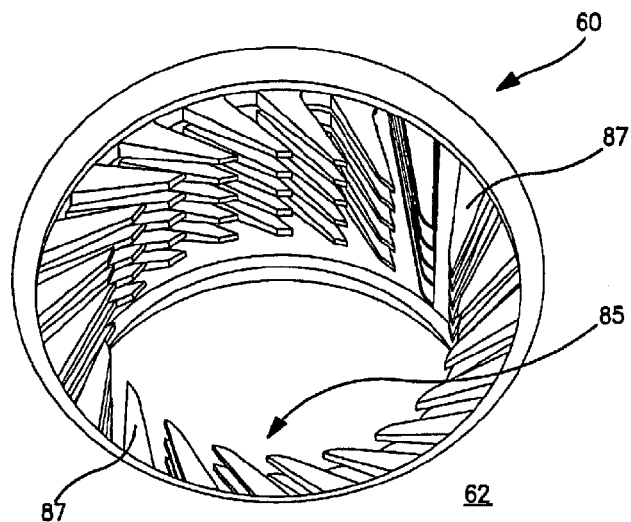
FIG. 8 is a top perspective view of a section of a fastener receiving member provided in accordance with the present disclosure.

Other aspects can be provided in accordance with the present disclosure that prevent fastener 10 from backing out of fastener receiving member 60, as shown in FIG. 8. Such prevention is desirable to avoid fastener 10 from becoming loose and thereby failing to maintain fastener receiving member 60 in a secure and fixed position. Furthermore, in anatomically critical areas, such as the anterior cervical spine, impingement of backed-out fastener 10 on overlying structures can create the risk of significant morbidity and mortality. Thus, an anti-unscrewing system is desirable to prevent unscrewing or backing out of fastener 10 from plate or fastener receiving member 60.

Figure 9:
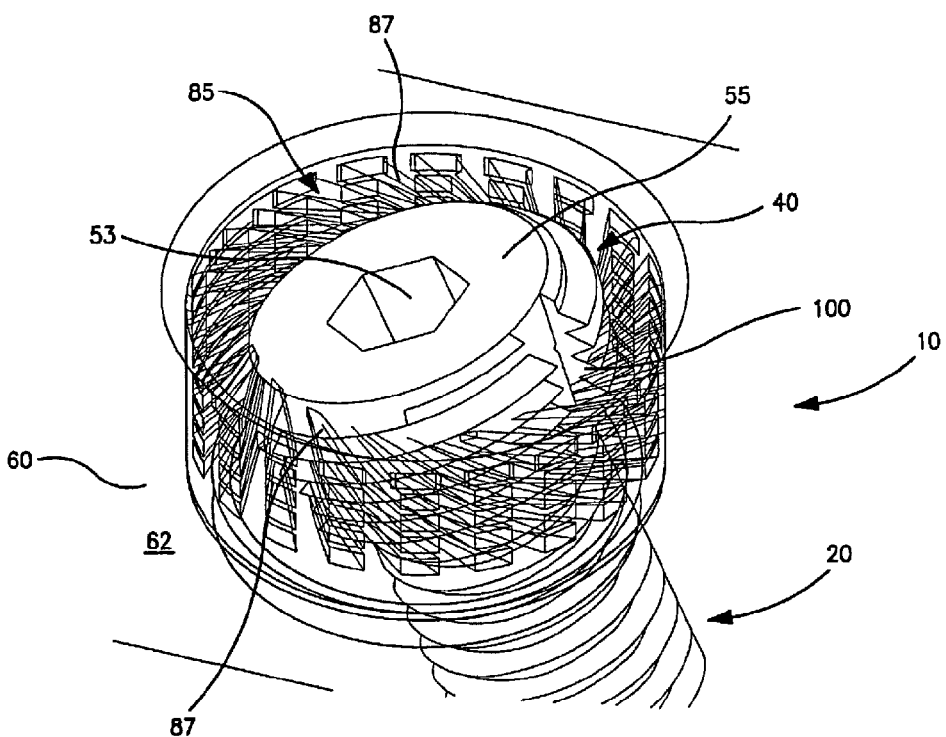
FIG. 9 is a top perspective view of a section of a fastener receiving member provided in accordance with the present disclosure in which the fastener comprises at least one slot for providing anti-unscrewing properties.
Figure 10:
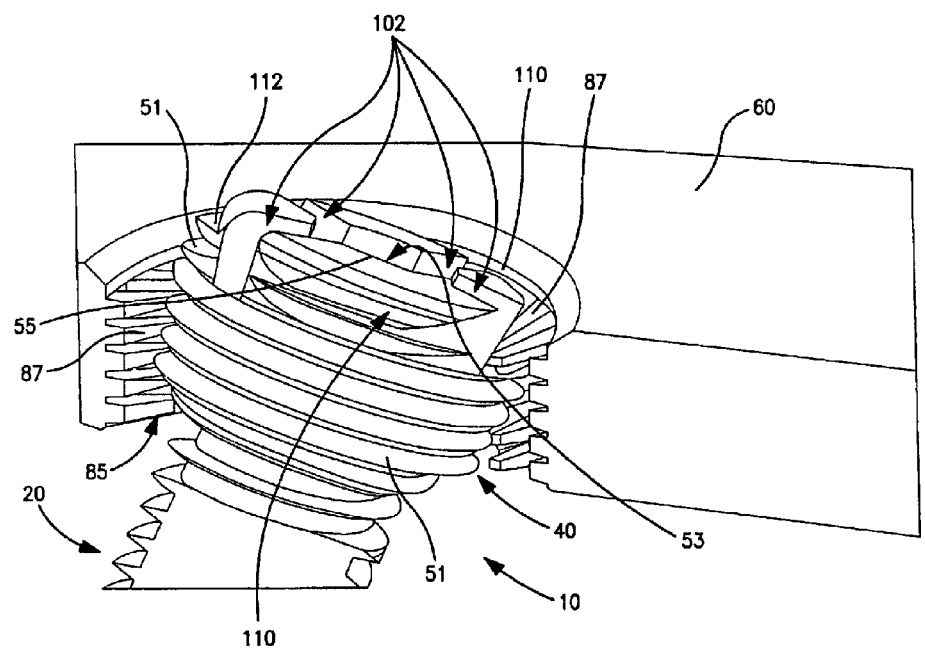
FIG. 10 is a partially cut away and vertical cross-sectional view illustrating a fastener having a plurality of fastener slots being positioned in the fastener receiving member provided in accordance with the present disclosure.

In one aspect for providing an anti-unscrewing function, as illustrated in FIG. 9, fastener 10 can include an at least one slot generally designated 100 that can be filled with protrusions 87 of contact region 85 of fastener receiving member 60 upon insertion of fastener 10 into contact region 85 of fastener receiving member 60, thereby preventing fastener 10 from unscrewing or backing out and serving to lock fastener 10 in a permanent manner. In other aspects of the present disclosure, as depicted in FIG. 10, fastener 10 can include a plurality of slots generally designated 102 such that protrusions 87 fill multiple slots 102 of fastener 10.

Figure 11:
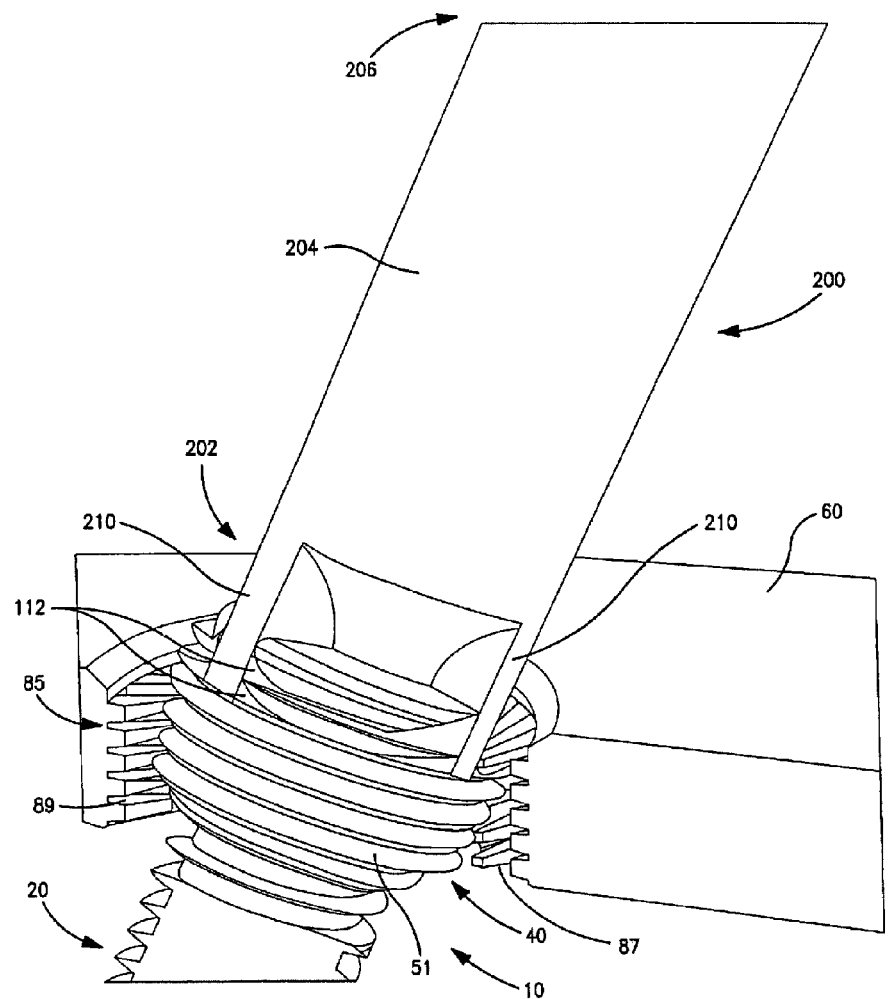
FIG. 11 is a partially cut away and vertical cross-sectional view of a bone screw/plate system for providing anti-unscrewing properties provided in accordance with the present disclosure.

In certain instances, though, removal of fastener 10 from the anti-unscrewing system as disclosed herein may be desirable or necessary. Thus, as shown in FIG. 11, a fastener driver generally designated 200 can be provided for inserting and removing fastener 10 from fastener receiving member 60 of the anti-unscrewing system. Fastener driver 200 can serve to deflect protrusions 87 out of the at least one slot 100 or plurality of slots 102 to facilitate insertion or removal of fastener 10 from contact region 85 of fastener receiving member 60.

Also, an angular driver tool generally designated 300 having an end portion designated 310 can be provided for improving angular adjustability and control of the insertion orientation of fastener 10. By providing tool 300 with a nipple 320 (FIGS. 13 and 14) integral therewith or a rod 340 (FIGS. 15 and 16) having a threaded end 342 that can extend within a cavity generally designated 48 (FIG. 12) of fastener 10, a surgeon can more precisely control the angle of insertion of fastener 10, while ensuring that fastener 10 will not separate from angular driver tool 300. In other words, fastener 10 will not fall off end portion 310 of tool 300 when the surgeon tilts tool 300 to insert fastener 10 at an angular orientation. In other aspects, the features of fastener driver 200 and angular tool 300 can be combined such that the combination provides improved angular insertion control of fastener 10 while also effectuating insertion and removal of a fastener used in an anti-unscrewing system as provided.

A. Anti-Unscrewing Fastener

With reference to FIG. 9, head section 40 of fastener 10 can include at least one slot 100 about its outer circumference that can extend from top surface 55 downward. Slot 100 can provide anti-unscrewing properties to prevent backing out of fastener 10 from fastener receiving member 60. Furthermore, slot 100 can extend downward the entire length of head section 40 or terminate lengthwise at any finite point along head section 40. Slot 100 can be of any width and depth. Protrusions 87 of fastener receiving member 60 can be angled such that protrusions 87 permit fastener 10 to rotate in one direction, but resist rotation in the opposite direction. To facilitate the turning of fastener 10 by the user thereof, head section 40 can include recess 53 for the insertion of an appropriate tool such as a screwdriver, key, or wrench. The shape of recess 53 can be a single or cross-shaped slot, a square, a hexagon, a star, or the like.

To prevent removal and backing out of fastener 10 protrusions 87 project into slot 100 such that fastener 10 will catch on and be engaged by protrusions 87 to prohibit reverse rotation or backing out of fastener 10. Attempting to remove fastener 10 in such embodiments requires a strong torsional force that can break protrusions 87, thereby littering the surgical field therewith, or that can bend protrusions 87 such that they would no longer function. Therefore, it would also be advantageous to have an instrument, such as fastener driver 200 discussed further below, that facilitates removal of fastener 10 having slot 100 from fastener receiving member 60.

In other aspects, such as shown in FIG. 10, head section 40 can include a plurality of spaced-apart slots 102. Slots 102 can provide anti-unscrewing properties to prevent backing out of fastener 10. Slots 102 can extend from top surface 55 of head section 40 of fastener 10 and downward and terminate at any length along head section 40. Slots 102 can also perform the same function as slot 100 in that protrusions 87 can project thereinto for effectuating non-rotational movement of fastener 10 in a reverse manner. Slots 102 can also extend radially inwardly within head section 40 to facilitate engagement of a screwdriver type tool for rotating fastener 10, thereby also forming a plurality of arcuate portions therebetween that are generally designated 110. Arcuate portions 110 can each also include an extension of second thread 51 thereon, which second thread 51 generally extends around the head of fastener 10. Second thread 51 can have a beveled portion generally designated 112 proximate to slots 102 to prevent second thread 51 from catching on protrusions 87. Slots 102 can be of any number, shape, and design. Also, slots 102 can terminate or transition into recess 53 of head section 40 for the insertion of an appropriate tool having a corresponding shape.

Figure 12:
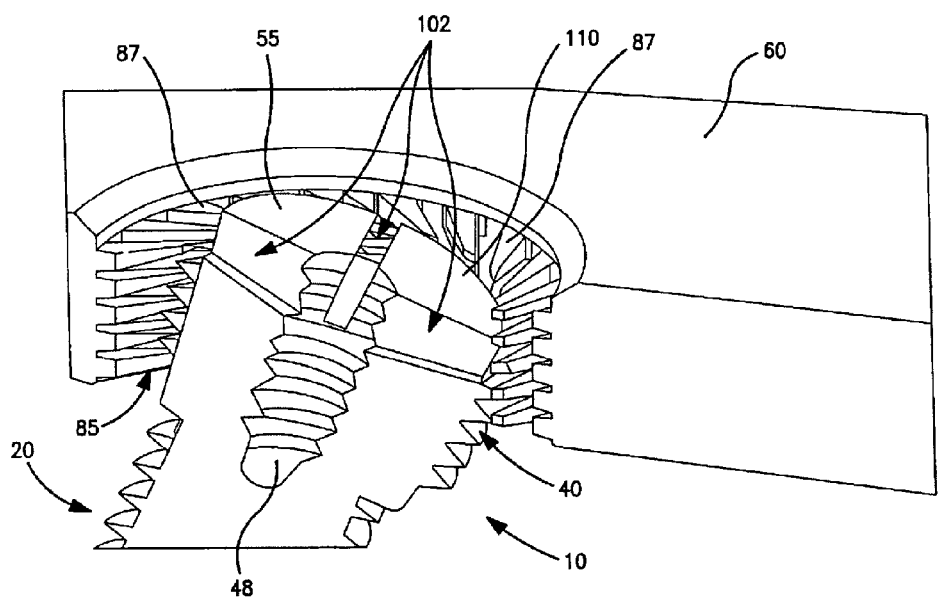
FIG. 12 is a partially cut away and vertical cross-sectional view of a fastener receiving member having a fastener positioned therein wherein the fastener has a cavity that can provide improved angular control of the fastener in accordance with the present disclosure.

In other aspects, rigid angular control of fastener 10 can be achieved by providing cavity 48 within fastener 10, as depicted in FIG. 12. Cavity 48 can be substantially elongate and can be configured to receive a screwdriver type instrument, for example, tool 300 as discussed further below. Cavity 48 can be threaded to matingly receive a threaded portion of tool 300, thereby allowing fastener 10 to be angled without risk of fastener 10 separating from and falling off of tool 300. Furthermore, cavity 48 can extend to any depth within fastener 48 and can be of any suitable shape and size. Also, cavity 48 can extend entirely through fastener 10 such that fastener 10 is cannulated for receiving a guide wire 400 and the like.

B. Anti-Unscrewing Driver

An instrument can be configured for use in inserting and removing fastener 10 from an anti-unscrewing system such as that in the present disclosure. Fastener driver 200 can be used to insert fastener 10 into fastener receiving member 60 to provide anti-unscrewing properties when fastener 10 includes slot 100 or slots 102. As shown in FIG. 11, fastener driver 200 can be substantially elongate.

In one aspect, driver 200 can include a fastener receiving end generally designated 202, an elongate shaft 204, and an operational end generally designated 206. Fastener receiving end 102 can include a plurality of slot engagement portions 210 that are sized so as to be fittingly received within slots 102 of head section 40 of fastener 10, such that rotational torque can be provided when fastener receiving end 202 is rotated. Furthermore, slot engagement portions 210 can prevent protrusions 87 from projecting into slots 102 during rotational advancement of fastener 10 by filling slots 102, thereby allowing fastener 10 to rotate within fastener receiving member 60 without protrusions 87 impeding rotation by catching in slots 102. Upon removal of driver 200, protrusions 87 can engage fastener 10 within slots 102 in an anti-unscrewing manner.

To remove fastener 10, slot engagement portions 210 of driver 200 can be inserted into slots 102, thereby deflecting protrusions 87 radially outwardly and out of slots 102. When protrusions 87 are no longer within slots 102 and impeding rotation, fastener 10 can be advanced outwardly from fastener receiving member 60 for removal of fastener 10 therefrom. As stated above, second thread 51 can have a beveled portion 112 to prevent protrusions 87 from catching thereon.

C. Angular Insertion Tool

Figure 14:
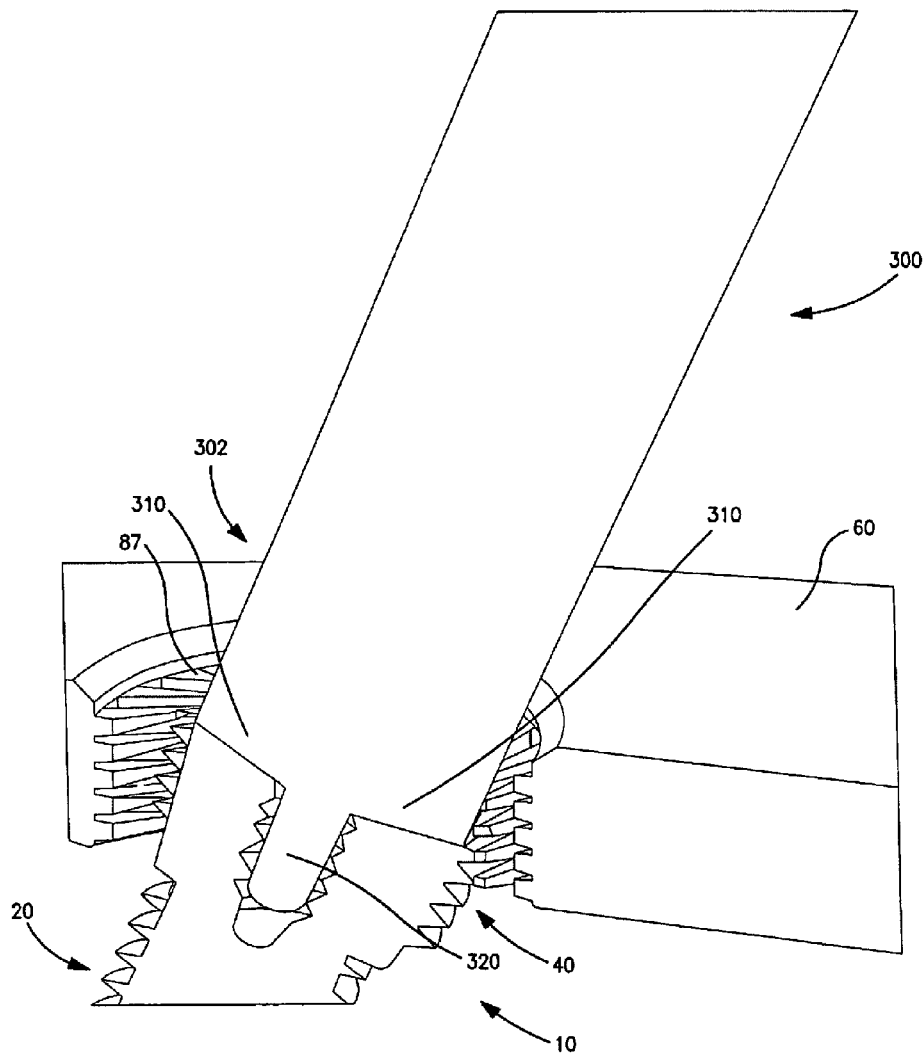
FIG. 14 is a vertical cross-sectional view illustrating the bone screw/plate system of FIG. 13 in which the fastener driver is shown in cross-section.
Figure 15:
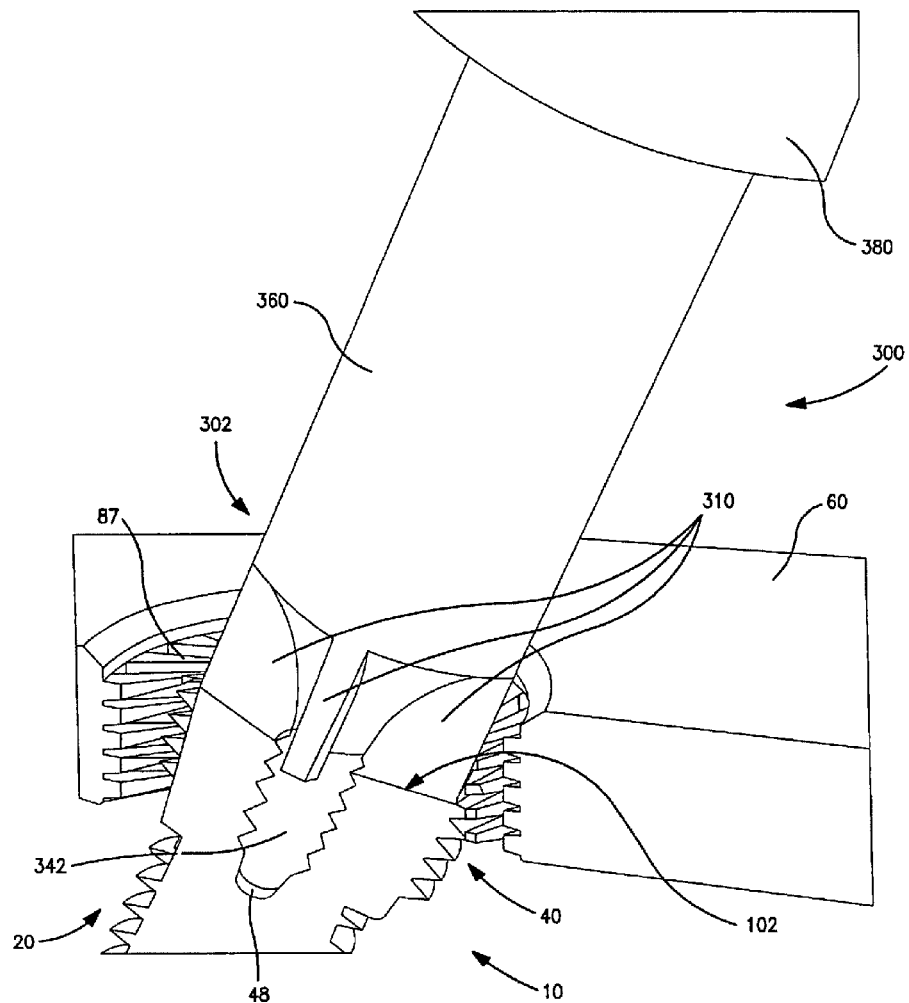
FIG. 15 is a partially cut away and vertical cross-sectional view illustrating another bone screw/plate system for providing anti-unscrewing properties and improved angular insertion control of a fastener in accordance with the present disclosure.
Figure 16:
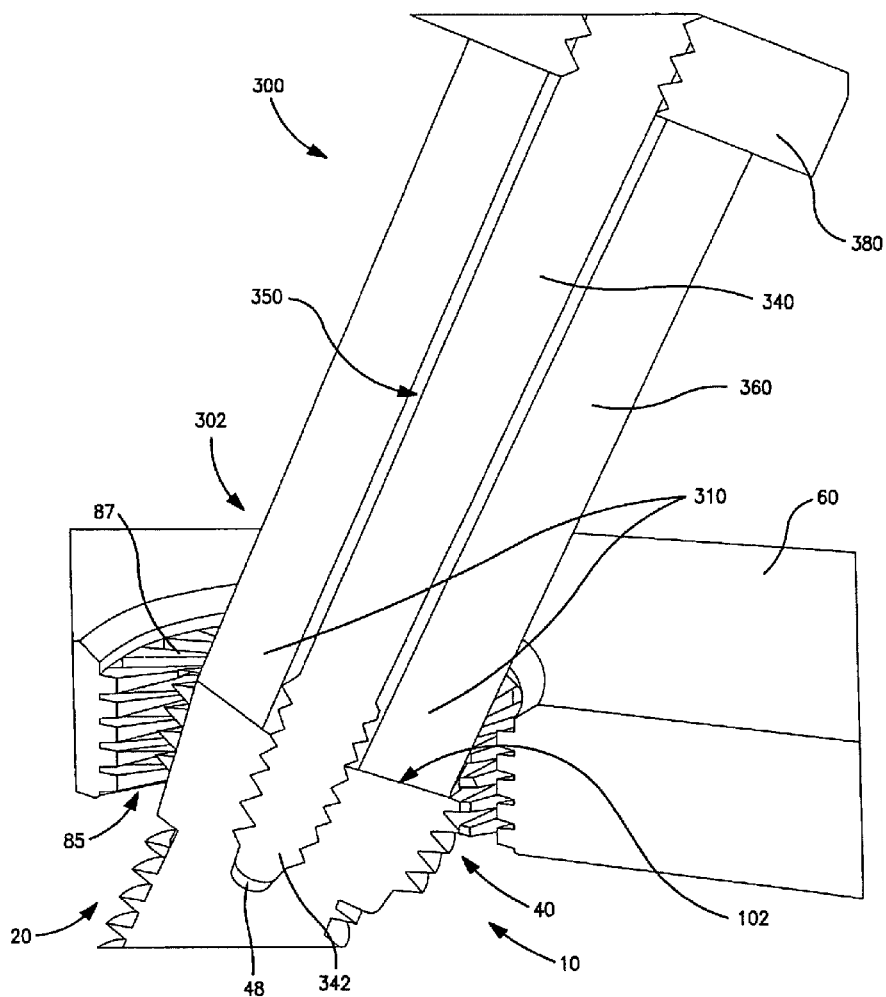
FIG. 16 is a vertical cross-sectional view illustrating the system of FIG. 15 in which the fastener driver is shown in cross-section.

Angular insertion of fastener 10 is often needed, including during use in the disclosed anti-unscrewing system. Angular driver tool 300 can be configured to provide improved rigid angular control of fastener 10 during angular insertion, as illustrated in FIGS. 14-16. Preventing fastener 10 from falling off tool 300 can be extremely important to the surgeon when attempting to insert fastener 10 at an angle. In one embodiment, slot engagement portions 310 can be substantially deep to prevent fastener 10 from slipping off of tool 300, and thus fastener receiving end 302 can lock angular direction in an improved manner.

Figure 13:
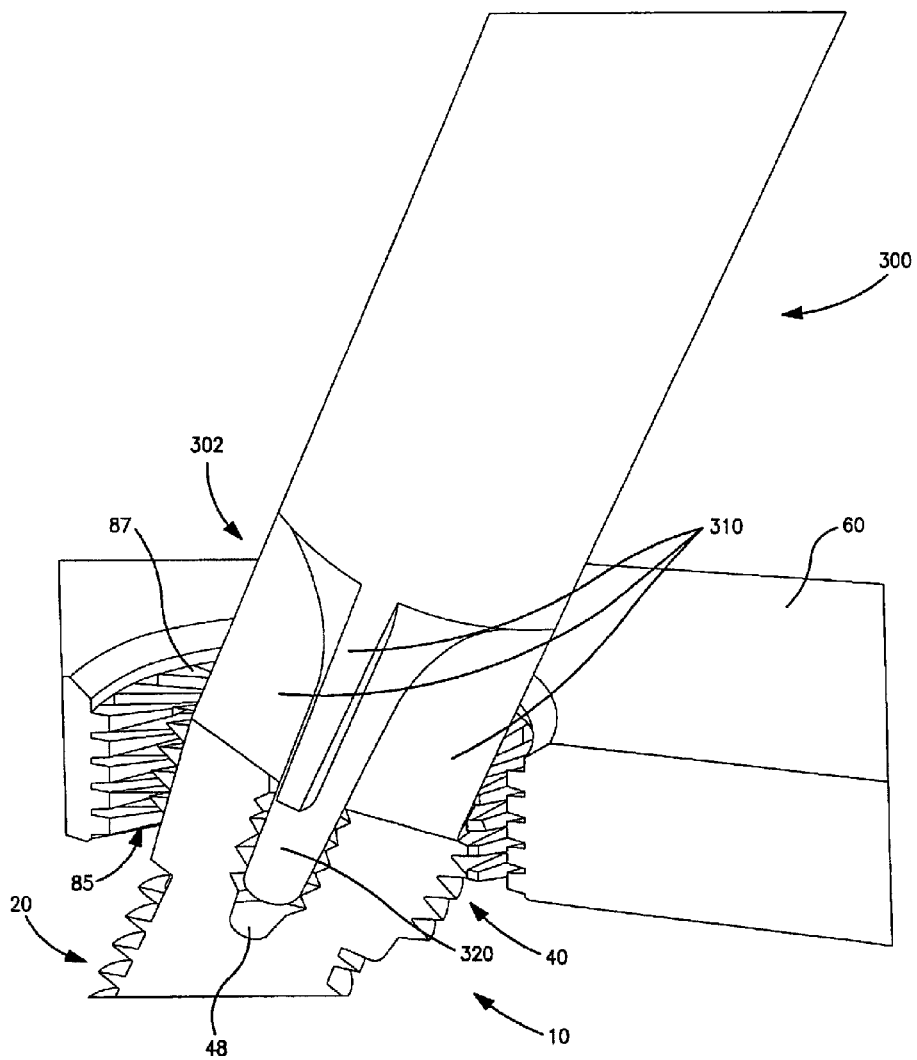
FIG. 13 is a partially cut away and vertical cross-sectional view illustrating a bone screw/plate system for providing anti-unscrewing properties and improved angular insertion control of a fastener in accordance with the present disclosure.

In other aspects, such as those illustrated in FIGS. 13 and 14, tool 300 can further include a nipple 320 that can be matingly received within cavity 48 of fastener 10. Insertion of nipple 320 within cavity 48 gives better control of fastener 10 than do simple cross head screwdrivers, from which fasteners can easily fall off, that are commonly used in surgical applications. Nipple 320 can be inserted into cavity 48 while slot engagement portions 310 are received within slots 102. Thus, the surgeon can angle tool 300 and fastener 10 without worry that fastener 10 will fall off end 302, thereby providing improved angular control to ensure that the correct insertion angle of fastener 10 is achieved. Nipple 320 can be threaded or not be threaded. Cavity 48 can be threaded or not be threaded. Furthermore, nipple 320 can assist the surgeon in holding tool 300 perfectly coaxial with fastener 10 to eliminate the possibility that tool 300 is not coaxial and that slots 102 are not filled by slot engagement portions 310, making fastener 10 difficult to unscrew due to protrusions 87 projecting into slots 102 in locked manner.

In yet another aspect, as shown in FIGS. 15 and 16, tool 300 can be configured to provide absolute rigid angular control of fastener 10 when the surgeon cannot afford for fastener 10 to separate from tool 300, such as during spinal applications. In such embodiments, tool 300 can include a driver rod 340 that can have a threaded end 342 for matingly engaging cavity 48. Cavity 48 can also be threaded to matingly receive threaded end 342. Tool 300 can include a sleeve portion 360 that can define a cannulated shaft generally designated 350 (FIG. 16) for receiving driver rod 340. Cannulated shaft 350 can extend entirely through tool 300. Driver rod 340 can have a ram 380 on the end opposite threaded end 342.

In use, driver rod 340 can be rotated into head section 40 of fastener 10 at cavity 48. Then, sleeve portion 360 can slide down over driver rod 340 such that slot engagement portions 310 of tool 300 fit into slots 102 in head section 40 of fastener 10, thereby providing torsional attachment such that fastener 10 can be turned during the action of driving fastener 10 into bone and into contact region 85 of fastener receiving member 60 and filling slots 102 such that protrusions 87 can no longer catch or project within slots 102 (which allows fastener 10 to be unscrewed when removal is required). Then, ram 380 can be threaded onto driver rod 340 so that when ram 380 is screwed forward it rams sleeve portion 360 down onto fastener 10, which is maintained in a fixed position because it is already fastened to driver rod 340. That is, fastener 10 can fasten onto driver rod 340, sleeve portion 360 can then slide down to give torsional control and fill slots 102, and then sleeve portion 360 can be held firmly in that position by ram 380.

Once fastener 10 is fastened into bone and contact region 85, ram 380 can be backed off, allowing sleeve portion 360 to be pulled back. As a result, protrusions 87 can drop into slots 102 so that fastener 10 will not back-out of fastener receiving member 60, thereby allowing the surgeon to unscrew driver rod 340 from fastener 10 without unscrewing fastener 10. When removal of fastener 10 is necessary, for example after healing, the surgeon can clean out soft tissue from within slots 102 of fastener 10, then screw in driver rod 340, then insert sleeve portion 360 to fill slots 102 and deflect protrusions 87, then lock tool 300 into place with ram 380, and then unscrew the entire assembly. Once ram 380, driver rod 340 and sleeve portion 360 are all assembled to fastener 10, they all can be configured to cooperatively function to rotate fastener 10 in an angular direction (i.e., they rotate together and act as one assembly).

Figure 17:
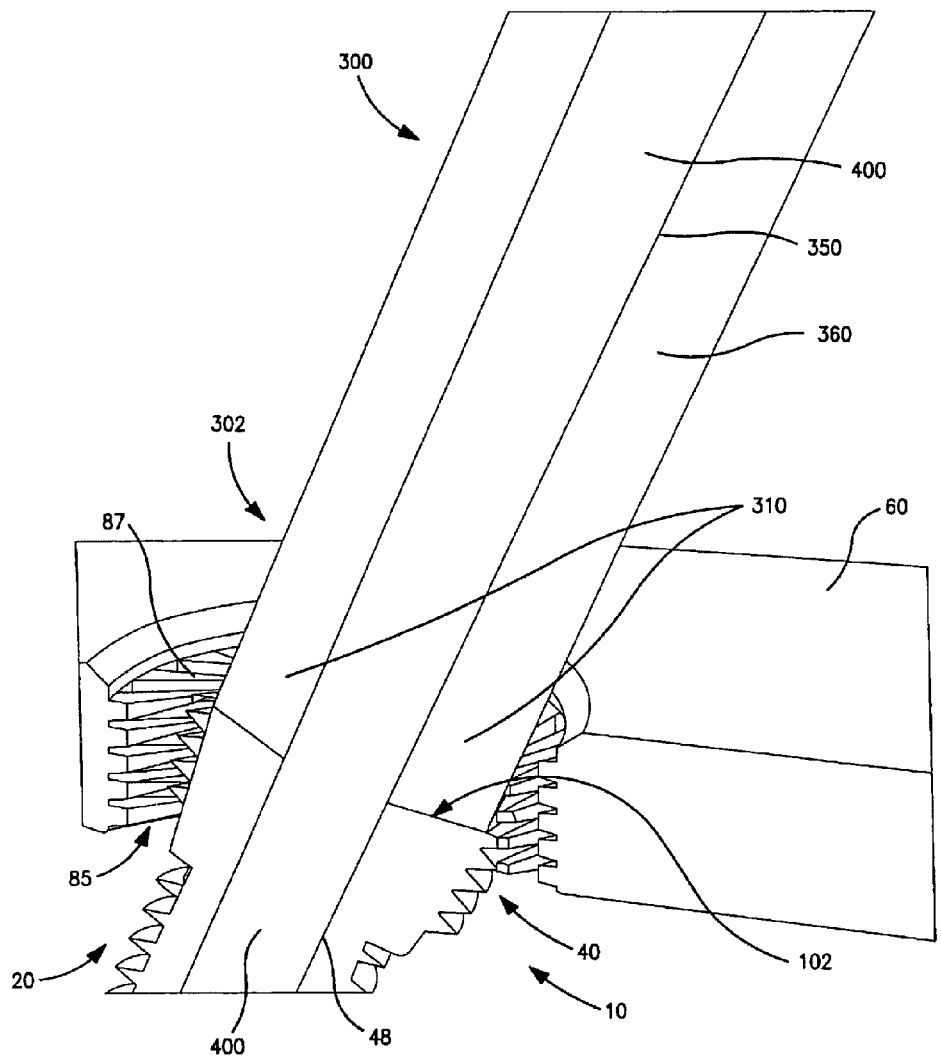
FIG. 17 is a partially cut away and vertical cross-sectional view illustrating an anti-unscrewing bone screw/plate system in use with a guide wire to control angular insertion of the fastener in accordance with the present disclosure.

In another aspect, as shown in FIG. 17, fastener 10 can be cannulated such that cavity 48 runs the entire length of fastener 10 and guide wire 400 can pass entirely through fastener 10 in a substantially coaxial manner. Tool 300 can include sleeve 360 that defines cannulated shaft 350 such that guide wire 400 can pass entirely therethrough in a substantially coaxial manner. Tool 300 can further include slot engagement portions 310 such that tool 300 can be used with the anti-unscrewing system as disclosed, while also providing improved angular insertion control. In use, the surgeon can first run guide wire 400 through contact region 85 having protrusions 87 into a predetermined location in bone that fastener 10 will enter, which can be confirmed with x-ray imaging. The surgeon can slide the cannulated fastener 10 over guide wire 400 and then slide tool 300 over guide wire 400, wherein tool 300 can then drive fastener 10. Guide wire 400 can provide the necessary alignment of all the elements rather than using nipple 320 or driver rod 340 to ensure fastener 10 remains on end portion 302 of tool 300 in the correct angular orientation.

D. Anti-Unscrewing and Angular Insertion Instrument

In other aspects, elements of fastener driver 200 and angular driver tool 300 can be combined such that the combination can produce instruments, as illustrated in FIGS. 13-17, having slot engagement portions 210, 310 to facilitate use with an anti-unscrewing system and that further provide rigid angular insertion control. In such embodiments, slot engagement portions 210, 310 can be coupled with nipple 320 or threaded end 342 of driver rod 340 to exhibit both anti-unscrewing and angular insertion properties.

It will be understood that various details of the present disclosure may be changed without departing from the scope of the present disclosure. Furthermore, the foregoing description is for the purpose of illustration only, and not for the purpose of limitation, as the present disclosure is defined by the claims as set forth hereinafter.

What is claimed is:

1. A surgical fastening apparatus adapted to provide anti-unscrewing features, comprising:
    (a) a fastener comprising an elongate section and an adjoining head section disposed along a fastener axis, the head section comprising a thread and an at least one slot defined in an outer periphery of the head section that extends therewithin; and
    (b) a fastener receiving member comprising first and second opposing major surfaces, an inside surface extending between the first and second major surfaces and defining an aperture generally coaxially disposed about an aperture axis, and a tappable contact region disposed on the inside surface, wherein the tappable contact region is extendable into the slot of the fastener to prevent backing out of the fastener and the tappable contact region is deflectable from the slot of the fastener to permit removal of the fastener;
    (c) wherein the tappable contact region comprises a plurality of protrusions extending inwardly from the inside surface of the fastener receiving member with the plurality of protrusions being angled to enter the slot of the fastener such that the protrusions permit the fastener to rotate in one direction, but resist rotation in the opposite direction to prevent backing out of the fastener.

2. The apparatus according to claim 1 wherein the at least one slot is a plurality of slots.

3. The apparatus according to claim 1 wherein the fastener is a surgical bone screw.

4. The apparatus according to claim 1 wherein the elongate section comprises a thread.

5. The apparatus according to claim 4 wherein the elongate section comprises a first outer surface, and the thread of the elongate section extends along a length of the first outer surface in generally helical relation to the fastener axis.

6. The apparatus according to claim 5 wherein the head section comprises a second outer surface, and the thread of the head section extends along a length of the second outer surface in generally helical relation to the fastener axis.

7. The apparatus according to claim 1 wherein the head section has a rounded vertical profile.

8. The apparatus according to claim 1 wherein the head section has a substantially hemispherical vertical profile.

9. The apparatus according to claim 1 wherein the head section has a substantially frusto-conical vertical profile.

10. The apparatus according to claim 1 wherein the head section has a converging/diverging vertical profile.

11. The apparatus according to claim 1 wherein the first and second major surfaces of the fastener receiving member define a surgical plate.

12. The apparatus according to claim 1 wherein the tappable contact region comprises an insert fitted to the inside surface.

13. The apparatus according to claim 1 wherein the plurality of protrusions extend generally radially inwardly from the inside surface, and wherein the tappable contact region comprises a plurality of interstices between the protrusions, whereby the plurality of protrusions project into the slot of the fastener to prevent backing out.

14. The apparatus according to claim 13 wherein the protrusions are constructed from a metal-containing material.

15. The apparatus according to claim 13 wherein the protrusions comprise a polymeric material.

16. The apparatus according to claim 1 wherein the fastener is inserted at an angle that ranges from approximately 0 to approximately 90 degrees.

17. A surgical anti-unscrewing system that provides anti-unscrewing features, comprising:
 (a) a fastener comprising an elongate section and an adjoining head section disposed along a fastener axis, the head section comprising a thread and an at least one slot defined in an outer periphery of the head section that extends therewithin;
 (b) a fastener receiving member comprising first and second opposing major surfaces, an inside surface extending between the first and second major surfaces and defining an aperture generally coaxially disposed about an aperture axis, and a tappable contact region comprising protrusions disposed on the inside surface, wherein the protrusions project into the at least one slot of the fastener, thereby preventing the fastener from backing out of the fastener receiving member; and
 (c) a fastener driver providing torsional force to the fastener and comprising first and second ends, wherein the first end comprises at least one slot engagement portion matingly receivable by the at least one slot of the fastener, whereby during insertion of the fastener by the fastener driver the at least one slot engagement portion prevents the protrusions from projecting into the at least one slot to facilitate insertion and during removal of the fastener the slot engagement portion deflects the protrusions out of the at least one slot to facilitate removal.

18. The system according to claim 17 wherein the fastener is a surgical bone screw.

19. The system according to claim 17 wherein the at least one slot is a plurality of slots.

20. The system according to claim 19 wherein the at least one slot engagement portion is a plurality of slot engagement portions.

21. The system according to claim 17 wherein the head section of the fastener defines a cavity that extends from the top of the head section to a finite point within the fastener.

22. The system according to claim 21 wherein the fastener driver further comprises a nipple extending from the first end and the nipple being received in the cavity in a substantially coaxial manner for controlling angular insertion of the fastener.

23. The system according to claim 22 wherein the nipple is threaded.

24. The system according to claim 21 wherein the cavity defined by the head section of the fastener is threaded.

25. The system according to claim 17 wherein the second end of the fastener driver comprises a handle to assist in rotating the fastener driver.

26. The system according to claim 24 wherein the fastener driver further comprises:
 (i) a sleeve portion connecting the first and second ends, the sleeve portion defining an elongate cannulated shaft that extends the entire length of the fastener driver;
 (ii) a driver rod having proximal and distal ends and being fittingly received within the elongate cannulated shaft, wherein the proximal and distal ends are threaded such that the proximal end threadingly engages the cavity; and
 (iii) a ram threadingly engaging the distal end of the driver rod and the ram being positioned proximate to the second end of the insertion tool.

27. The system according to claim 17 wherein the fastener driver further comprises a sleeve portion connecting the first and second ends, the sleeve portion defining an elongate cannulated shaft that extends the entire length of the fastener driver.

28. The system according to claim 27 wherein the fastener is cannulated such that the fastener defines a cavity that extends from the top of the head portion entirely through the fastener.

29. The system according to claim 28 wherein the fastener driver permits a guide wire to extend through the fastener and fastener driver for alignment.

30. A surgical method for affixing a fastener to a fastener receiving member such that the fastener will not back-out of the fastener receiving member, comprising:
 (a) providing a fastener comprising an elongate section and an adjoining head section disposed along a fastener axis, the head section comprising a thread and at least one slot defined in an outer periphery of the fastener and that extends therewithin;
 (b) providing a fastener receiving member comprising first and second opposing major surfaces, an inside surface extending between the first and second major surfaces and defining an aperture generally coaxially disposed about an aperture axis, and a tappable contact region disposed on the inside surface;
 (c) selecting an insertion angle at which the fastener is to be inserted in relation to the fastener receiving member, wherein the insertion angle is defined between the fastener axis and the aperture axis;
 (d) inserting the elongate section of the fastener through the aperture until the thread of the head section contacts the tappable contact region; and
 (e) tapping the fastener into the fastener receiving member such that the fastener is oriented at the selected insertion angle by threading the thread of the head section into the tappable contact region while the fastener is oriented at the selected insertion angle, and wherein the tappable contact region engages the at least one slot after insertion to prevent backing out of the fastener by a portion of the tappable contact region extending into the slot of the fastener.

31. The method according to claim 30 comprising placing one of the major surfaces of the receiving member against bone material, and inserting the elongate section of the fastener into the bone material.

32. The method according to claim 31 wherein the elongate section is threaded, and inserting the elongate section into the bone material comprises threading the elongate section into the bone material.

33. The method according to claim 32 wherein threading of the elongate section further into the bone material causes threading of the thread of the head section into the tappable contact region of the receiving member.

34. The method according to claim 30 wherein the tappable contact region comprises a plurality of protrusions extending generally radially inwardly from the inside surface and a plurality of interstices between the protrusions, and wherein the protrusions project within the at least one slot to prevent backing out of the fastener.

35. The method according to claim 34 wherein inserting the fastener comprises using a fastener driver comprising first and second ends, wherein the first end comprises at least one slot engagement portion matingly receivable by the at least one slot of the fastener, whereby during insertion of the fastener the at least one slot engagement portion of the fastener driver prevents the protrusions from projecting into the at least one slot to facilitate rotational advancement of the fastener.

36. The method according to claim 34 further comprising:
(f) removing the fastener using a fastener driver comprising first and second ends, wherein the first end comprises at least one slot engagement portion matingly receivable by the at least one slot of the fastener, whereby during removal of the fastener the at least one slot engagement portion of the fastener driver deflects the protrusions out of the at least one slot to facilitate removal.

37. The system according to claim 4 wherein the tappable contact region is tappable by the thread of the elongate section of the fastener.

38. The system according to claim 37 wherein the fastener is affixable to the tappable contact region at a selected one of a plurality of different insertion angles that can be selectively formed between the fastener axis and the aperture axis.

39. The system according to claim 17 wherein the thread of the elongate section of the fastener includes an external thread with the tappable contact region being tappable by the thread of the elongate section of the fastener.

40. The system according to claim 39 wherein the fastener is affixable to the tappable contact region at a selected one of a plurality of different insertion angles that can be selectively formed between the fastener axis and the aperture axis.

41. A surgical fastening apparatus adapted to provide anti-unscrewing features, comprising:
(a) a fastener comprising an elongate section with an external thread and an adjoining head section disposed along a fastener axis, the head section comprising a thread and at least one slot defined in an outer periphery of the head section that extends therewithin; and
(b) a fastener receiving member comprising first and second opposing major surfaces, an inside surface extending between the first and second major surfaces and defining an aperture generally coaxially disposed about an aperture axis, and a tappable contact region disposed on the inside surface;
(c) wherein the tappable contact region is formed so as to allow for being tapped by the external thread of the elongate section of the fastener to affix the fastener to the tappable contact region at a selected one of a plurality of different insertion angles that can be selectively formed between the fastener axis and the aperture axis; and
(d) wherein the tappable contact region comprises a plurality of protrusions extendable into the slot of the fastener to prevent backing out of the fastener and the tappable contact region is deflectable from the slot of the fastener to permit removal of the fastener.

42. The apparatus according to claim 41 wherein the at least one slot is a plurality of slots.

43. The apparatus according to claim 41 wherein the fastener is a surgical bone screw.

44. The apparatus according to claim 1 wherein the plurality of protrusions are extendable into the slot of the fastener such that the protrusions prevent backing out of the fastener and the plurality of protrusions being deflectable from the slot of the fastener to permit removal of the fastener.

* * * * *